(12) United States Patent
Barran et al.

(10) Patent No.: US 12,354,864 B2
(45) Date of Patent: Jul. 8, 2025

(54) BIOMARKERS AND USES THEREOF

(71) Applicant: The University of Manchester, Manchester (GB)

(72) Inventors: Perdita Barran, Manchester (GB); Depanjan Sarkar, Manchester (GB); Drupad Trivedi, Manchester (GB); Tilo Kunath, Manchester (GB); Joy Milne, Manchester (GB); Eleanor Sinclair, Manchester (GB)

(73) Assignee: The University of Manchester, Manchester (GB)

( * ) Notice: Subject to any disclaimer, the term of this patent is extended or adjusted under 35 U.S.C. 154(b) by 1116 days.

(21) Appl. No.: 17/263,456

(22) PCT Filed: Aug. 1, 2019

(86) PCT No.: PCT/GB2019/052169
§ 371 (c)(1),
(2) Date: Jan. 26, 2021

(87) PCT Pub. No.: WO2020/025967
PCT Pub. Date: Feb. 6, 2020

(65) Prior Publication Data
US 2021/0287894 A1 Sep. 16, 2021

(30) Foreign Application Priority Data
Aug. 1, 2018 (GB) .................... 1812561

(51) Int. Cl.
*A61K 9/00* (2006.01)
*G01N 1/40* (2006.01)
(Continued)

(52) U.S. Cl.
CPC .............. *H01J 49/26* (2013.01); *G01N 1/405* (2013.01); *G01N 1/4055* (2013.01);
(Continued)

(58) Field of Classification Search
CPC .................................................. G01N 33/5038
See application file for complete search history.

(56) References Cited

U.S. PATENT DOCUMENTS 11,139,156 B2  10/2021  Balog et al.
12,087,566 B2   9/2024  Eberlin et al.
(Continued)

FOREIGN PATENT DOCUMENTS

EP    1901064 A2     3/2008
JP    2015/055620    3/2015
(Continued)

OTHER PUBLICATIONS

Zhang et al., "Development of a Paper Spray Mass Spectrometry Cartridge with Integrated Solid Phase Extraction for Bioanalysis," Analytical Chemistry, vol. 87:6212-6219, May 2015.
(Continued)

*Primary Examiner* — Paul W Dickinson
(74) *Attorney, Agent, or Firm* — Hamilton, Brook, Smith & Reynolds, P.C.

(57) ABSTRACT

The present invention relates to methods of assessing whether an individual has Parkinson's Disease (PD) and/or is no longer responding to treatment, the method comprising the identification of one or more volatile compounds in the sebum of the individual. The present invention also relates to methods of extracting and detecting analytes from sebum.

7 Claims, 28 Drawing Sheets

(51) Int. Cl.
  *G01N 33/487* (2006.01)
  *H01J 49/26* (2006.01)
(52) U.S. Cl.
  CPC ... *G01N 33/487* (2013.01); *G01N 2001/4061* (2013.01); *G01N 2800/2835* (2013.01)

(56) References Cited

U.S. PATENT DOCUMENTS

| | | |
|---|---|---|
| 2016/0220557 A1 | 8/2016 | Esler et al. |
| 2016/0334381 A1 | 11/2016 | King-Smith et al. |
| 2017/0125228 A1 | 5/2017 | Bango et al. |
| 2023/0077659 A1 | 3/2023 | Barran et al. |
| 2023/0080918 A1 | 3/2023 | Barran et al. |

FOREIGN PATENT DOCUMENTS

| | | |
|---|---|---|
| JP | 2018-517120 A | 6/2018 |
| JP | 2019-534724 A | 12/2019 |
| WO | WO-2006/092689 | 9/2006 |
| WO | WO-2016/130646 | 8/2016 |
| WO | WO 2018132746 A1 | 7/2018 |
| WO | WO 2020025967 A1 | 2/2020 |
| WO | WO 2021156637 A1 | 8/2021 |
| WO | WO 2021156638 A1 | 8/2021 |
| WO | 2011/154261 A9 | 1/2025 |

OTHER PUBLICATIONS

Destaillats et al., "Identification of Δ6-monounsaturated fatty acids in human hair and nail samples by gas-chromatography-mass-spectrometry using ionic-liquid coated capillary column," Journal of Chromatography A, vol. 1218(2011):9394-9389, Nov. 2011.
Abu-Farha M, et al., "The role of lipid metabolism in Covid-19 virus infection and as a drug target," Int J Mol Sci 2020; 21.
Camera, et al., "Use of lipidomics to investigate sebum dysfunction in juvenile acne," Journal of Lipid Research, vol. 57, No. 6, Jun. 1, 2016 (Jun. 1, 2016), pp. 1051-1058.
Cody, R. B., et al., "Versatile new ion source for the analysis of materials in open air under ambient conditions," Anal. Chem. 2005, 77 (8), 2297-2302.
Cooks, R. G.; Ouyang, Z.; Takats, Z.; Wiseman, J. M., "Ambient Mass Spectrometry," Science (Washington, DC, U.S.) 2006, 311 (5767), 1566-1570.
De Silva IW, et al., "Paper spray mass spectrometry utilizing Teslin® substrate for rapid detection of lipid metabolite changes during Covid-19 infection," Analyst 2020; 145.
Esler WP, et al., "Human sebum requires de novo lipogenesis, which is increased in acne vulgaris and suppressed by acetyl-CoA carboxylase inhibition," Sci Transl Med 2019; 11: 1-14.
Eyre MT, et al., "Impact of baseline cases of cough and fever on UK Covid-19 diagnostic testing rates: estimates from the Bug Watch community cohort study," medRxiv 2020; : 2020.09.03.20187377.
Fall F, et al., "A split-range acquisition method for the non-targeted metabolomic profiling of human plasma with hydrophilic interaction chromatography—high-resolution mass spectrometry," J Chromatogr B Anal Technol Biomed Life Sci 2019; 1128: 121780.
Fonn, J. B.; Mann, M.; Mong, C. K.; Wong, S. F.; Whitehouse, C. M., "Electrospray ionization for mass spectrometry of large biomolecules," Science (Washington, D. C., 1883-) 1989, 246(4926), 64-71.
Gabelica, V., et al., "Recommendations for reporting ion mobility Mass Spectrometry measurements," Mass Spectrom. Rev. 2019, 38 (3), 291-320.
Hillenkamp, F.; Karas, M.; Beavis, R. C.; Chait, B. T., "Matrix-assisted laser desorption/ionization mass spectrometry of biopolymers," Anal. Chem. 1991, 63 (24), 1193A-1203A.
Y-C Huang, et al., "Predicting Breast Cancer by Paper Spray Ion Mobility Spectrometry Mass Spectrometry and Machine Learning," Analytical Chemistry, vol. 92, No. 2, Dec. 6, 2019 (Dec. 6, 2019), pp. 1653-1657.

Jackson, A. T., et al., "Microstructural and conformational studies of polyether copolymers," Int. J. Mass Spectrom. 2004, 238 (3), 287-297.
Jendrny P, et al., "Scent dog identification of samples from Covid-19 patients—A pilot study," BMC Infect Dis 2020; 20: 1-7.
Kendall, et al., "Lipidomics for translational skin research: A primer for the uninitiated," Experimental Dermatology, vol. 27, No. 7, May 7, 2018 (May 7, 2018), pp. 721-728.
Kobayashi T, Voisin B, Kim DY, et al., "Homeostatic Control of Sebaceous Glands by Innate Lymphoid Cells Regulates Commensal Bacteria Equilibrium," Cell 2019; 176: 982-997.e16.
Knight SR, et al., "Risk stratification of patients admitted to hospital with covid-19 using the ISARIC WHO Clinical Characterisation Protocol: development and validation of the 4C Mortality Score," BMJ 2020; 370: m3339.
Krechmer, Jordan, et al., "Real Time Lipidomic Profiling Using Desorption Ionization with Ion Mobility MS," Metabolomics and Lipidomics Applications, Feb. 1, 2016 (Feb. 1, 2016), pp. 275-281.
Manicke, N. E.; Belford, M., "Separation of Opiate Isomers Using Electrospray Ionization and Paper Spray Coupled to High-Field Asymmetric Waveform Ion Mobility Spectrometry," J. Am. Soc. Mass Spectrom. 2015, 26 (5), 701-705.
Myung, S., et al., "Coupling Desorption Electrospray Ionization with Ion Mobility/Mass Spectrometry for Analysis of Protein Structure: Evidence for Desorption of Folded and Denatured States," J. Phys. Chem. B 2006, 110 (10), 5045-5051.
Ohene, A., "Paws for thought: dogs sniff out Parkinson's disease with 90% hit rate," Parkinson's Life, Retrieved from the Internet: URL:https://parkinsonslife.cu/paws-for-thought-dogs-sniff-out-parkinsons-disease-with-90-hit-rate/[retrieved on Oct. 25, 2018] (2016).
Overmyer KA, Shishkova E, Miller IJ, et al., "Large-scale Multi-omic Analysis of Covid-19 Severity," Cell Syst 2020; 12:23-40.
Ranninger C, et al., "Improving global feature detectabilities through scan range splitting for untargeted metabolomics by high-performance liquid chromatography—Orbitrap mass spectrometry," Anal Chim Acta 2016; 930: 13-22.
Rohart F, ct al., "mixOmics: An R package for 'omics feature selection and multiple data integration," PLoS Comput Biol 2017; 13. 001:10.1371/journal.pcbi.1005752.
Ruszkiewicz OM, Sanders D, O'Brien R, et al., "Diagnosis of Covid-19 by analysis of breath with gas chromatography-ion mobility spectrometry—a feasibility study," EClinicalMedicine 2020.
Sarkar, D., et al., "Rapid Diagnosis of Parkinson's Disease from Sebum using Paper Spray Ionisation flon Mobility Mass Spectrometry," pp. 1-16, [Retrieved from the Internet: URL:http://itempdf74155353254prod.s3.amazonaws.com/12517385/Rapid Diagnosis of Parkinson s Disease from Sebum using Paper Spray Ionisation Ion Mobility-Mass Spectrometry-v1.pdf] [retrieved on Apr. 29, 2021] (2020).
Shetagc SS, ct al., "Application of scbomics for the analysis of residual skin surface components to detect potential biomarkers of type-1 diabetes mellitus," Sci Rep 2017; 7: 1-8.
Sinclair, E., et al., "Sebum: a window into dysregulation of mitochondrial metabolism in Parkinson's disease," pp. 1-20 [Retrieved from the Internet: URL:https://chemrxiv.org/articles/preprint /Sebum a Window into Dysregulation of Mito chondrTaT Metabolism-in Parkinson s DTseas e/11603613/1] [retrieved on Apr. 29, 2021] Preprint (2020).
Sinclair, E., et al., "Sebum: a window into dysregulation of mitochondrial metabolism in Parkinson's disease," pp. 1-32 ChemRxiv, [Retrieved from the Internet: URL:https://chemrxiv.org/articles/preprint /Sebum a Window into Dysregulation of Mito chondrTaT Metabolism-in Parkinson s DTseas e/11603613/1] [retrieved on Apr. 29, 2021] (2020).
Song JW, Lam SM, Fan X, et al., "Omics-Driven Systems Interrogation of Metabolic Dysregulation in Covid-19 Pathogenesis," Cell Metab 2020; 32: 188-202.e5.
Struwe W, et al., "The Covid-19 MS Coalition-accelerating diagnostics, prognostics, and treatment," Lancet 2020; 395: 1761-2.
Takats, Z., et al.. , "Mass Spectrometry Sampling Under Ambient Conditions with Desorption Electrospray Ionization," Science (Washington, DC, U. S.) 2004, 306 (5695), 471-473.

(56) References Cited

OTHER PUBLICATIONS

Wagner J., et al., "Absolute lymphocyte count is a prognostic marker in Covid-19: A retrospective cohort review," Int J Lab Hematol 2020; n/a. 001:10.1111/ijlh.13288.
Wenham C., et al., "Covid-19: the gendered impacts of the outbreak," Lancet 2020; 395: 846-8.
Wei X, et al., "Hypolipidemia is associated with the severity of Covid-19," J Clin Lipidol 2020; 14: 297-304.
WHO. "WHO advice for international travel and trade in relation to the outbreak of pneumonia caused by a new coronavirus in China," 2019. https://www.who.int/news-room/articles-detail/who-advice-for-international-travel-and-trade-in-relation-to-the-outbreak-of-pneumonia-caused-by-a-new-coronavirus-in-china (accessed Jul. 27, 2020).
WHO. Novel Coronavirus—China. 2020. https://www.who.int/csr/don/12-january-2020-novel-coronavirus-china/en/ (accessed Jul. 27, 2020).
WHO. "Simulation of the effects of Covid-19 testing rates on hospitalizations," https://www.who.int/bulletin/volumes/98/5/20-258186/en/ (accessed Sep. 29, 2020).
Wu D, Shu T, Yang X, et al., "Plasma metabolomic and lipidomic alterations associated with Covid-19," Natl Sci Rev 2020; 7: 1157-68.
Yap BW, et al., "Comparisons of various types of normality tests," J Stat Comput Simul 2011; 81: 2141-55.
International Preliminary Report on Patentability for International Application No. PCT/GB2019/052169, entitled "Biomarkers and Uses Thereof," Date Mailed Feb. 2, 2021.
Herrington et al., Electronic cigarette solutions and resultant aerosol profiles. Journal of chromatography A, vol. 1418:192-199, Sep. 2015.
Ishibe et al., Detection of gas components as a novel diagnostic method for colorectal cancer, Annals of Gastroenterological Surgery, vol. 2:147-153, Nov. 2017.
Krestin, The Seborrhoeic Facies as a Manifestation of Post-Encephalitic Parkinsonism and Allied Disorders, QJM: An International Journal of Medicine, vol. os-21(81):177-186, Jul. 1927.
Lawal et al., Headspace volatile organic compounds from bacteria implicated in ventilator-associated pneumonia analysed by TD-GC/MS, Journal of breath research, vol. 12(2):026002, Jan. 2018.
Liu et al., An Electronic Nose Based Beverage Identification using an Improved Fisher Discriminate Analysis Method, International Journal of Simulation Systems, Science & Technology, vol. 18(2):9. 1-9.6, Jun. 2017.
Morgan, Joy of super smeller: sebum clues for PD diagnostics, the Lancet Neurology, vol. 15(2):138-139, Feb. 2016.
Pizzini, et al., Analysis of volatile organic compounds in the breath of patients with stable or acute exacerbation of chronic obstructive pulmonary disease, Journal of breath research, vol. 12(2018):036002, Mar. 2018.
Rattray et al., Taking your breath away: metabolomics breathes life in to personalized medicine. Trends in Biotechnology, vol. 32(10): 538-548, Oct. 2014.
Rosier et al., Development and validation of a new TD-GC/MS method and its applicability in the search for human and animal decomposition products, Analytical and bioanalytical chemistry, vol. 406(15):3611-3619, Mar. 2014.
Sariol et al., Characterization of the exhaustion profile of activated carbon in industrial rum "filters" based on TGA, TD-GC/MS, colorimetry and NMR relaxometry, Materials Today Communications, vol. 11:1-10, Feb. 2017.
Shirasu et al., The scent of disease: volatile organic compounds of the human body related to disease and disorder, the Journal of Biochemistry, vol. 150(3):257-266, Jul. 2011.
Trivedi et al., Discovery of Volatile Biomarkers of Parkinson's Disease from Sebum, ACS Cent Sci. vol. 5(4): 599-606, Apr. 2019.
Wikoff et al., Metabolomics analysis reveals large effects of gut microflora on mammalian blood metabolites, Proceedings of the National Academy of Sciences, vol. 106(10): 3698-3703, Mar. 2009.
Wood-Kaczmar et al., Understanding the molecular causes of Parkinson's disease, Trends in molecular medicine, vol. 12(11): p. 521-528, Oct. 2006.
Xie et al., Analysis of changes in volatile constituents and expression of genes involved in terpenoid metabolism in oleocellosis peel, Food chemistry, vol. 243: p. 269-276, Sep. 2018.
International Search Report issued on International Patent Application No. PCT/GB2019/052169, dated Oct. 31, 2019.
Kolter, Ganglioside Biochemistry, International Scholarly Research Network, ISRN Biochemistry, Article ID 506160, 1-36, 2012.
Schnaar et al., Glycosphingolipids, Essentials of Glycobiology [Internet]. 4th edition, Chapter 11, Varki A, Cummings RD, Esko JD, et al., editors. Cold Spring Harbor (NY): Cold Spring Harbor Laboratory Press; 2022), 1-12.
Abedi et al., The survey of analytical methods for sample preparation and analysis of fragrances in cosmetics and personal care products, TrAC Trends in Analytical Chemistry, vol. 102:41-59, Feb. 2018.
Chang et al., Analysis of volatile organic compounds in exhaled breath for lung cancer diagnosis using a sensor system, Sensors and Actuators B: Chemical, vol. 255:800-807, Jul. 2017.
Cheng et al., Clinical Progression in Parkinson's Disease and the Neurobiology of Axons, Annals of Neurology, vol. 67(6):715-725, Jun. 2010.
DeMaagd et al., Parkinson's Disease and Its Management: Part 1: Disease Entity, Risk Factors, Pathophysiology, Clinical Presentation, and Diagnosis, Pharmacy and Therapeutics, vol. 40(8):504-532, Aug. 2015.
Donadio et al., Skin nerve alpha-synuclein deposits: a biomarker for idiopathic Parkinson disease, Neurology, vol. 82(15):1362-9, Mar. 2014.
Dunn et al., Systems level studies of mammalian metabolomes: the roles of mass spectrometry and nuclear magnetic resonance spectroscopy, Chem Soc Rev, vol. 40(1): 387-426, Feb. 2011.
Gatzias et al., Characterization and differentiation of sheep's milk from Greek breeds based on physicochemical parameters, fatty acid composition and volatile profile, Journal of the Science of Food and Agriculture, vol. 98(10):3935-3942 Aug. 2018.
Gerhardt et al., Volatile Compound Fingerprinting by Headspace Gas Chromatography-Ion Mobility Spectrometry (HS-GC-IMS) for the Authenticity Assessment of Honey as Benchtop Alternative to 1H-NMR Profiling, Analytical chemistry, Jan. 2018.
Goodacre et al., Proposed minimum reporting standards for data analysis in metabolomics, Metabolomics, vol. 3(3): 231-241, Aug. 2007.

| Correct classification rate 85% | Observed Control | Observed PD |
|---|---|---|
| Predicted Control | 0.67 | 0.33 |
| Predicted PD | 0.10 | 0.90 |

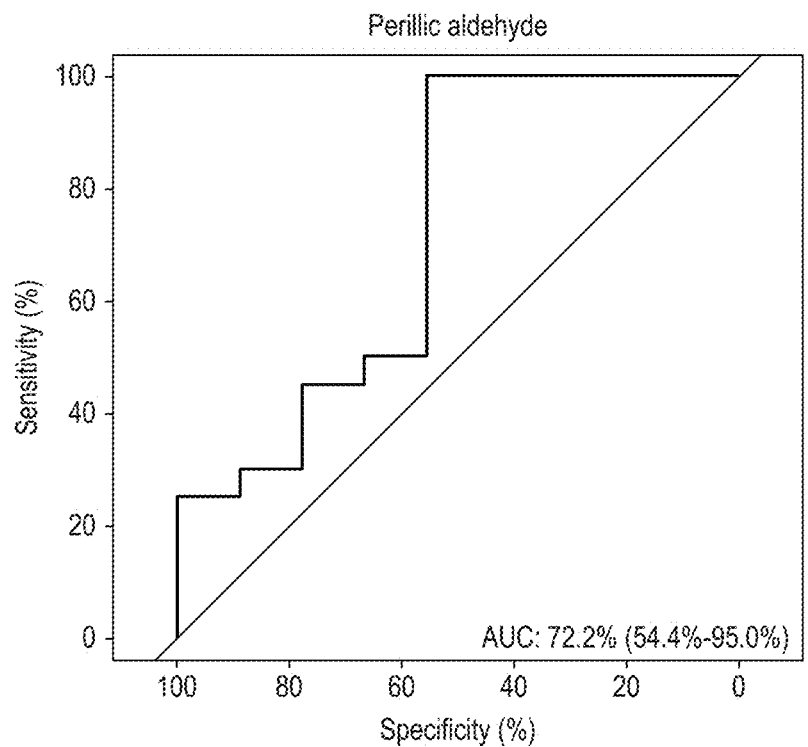
FIG. 2A(i)
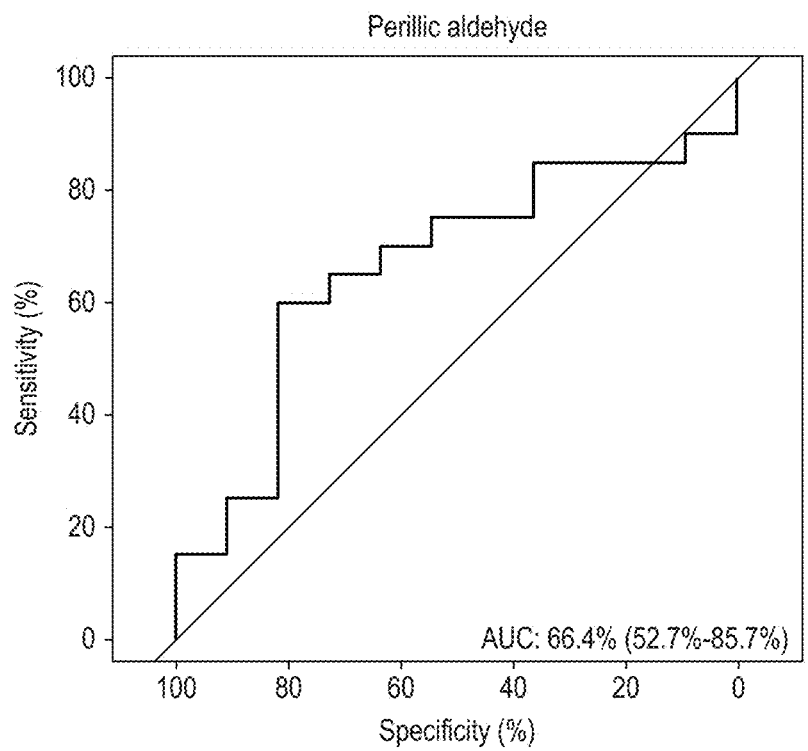
FIG. 2A(ii)

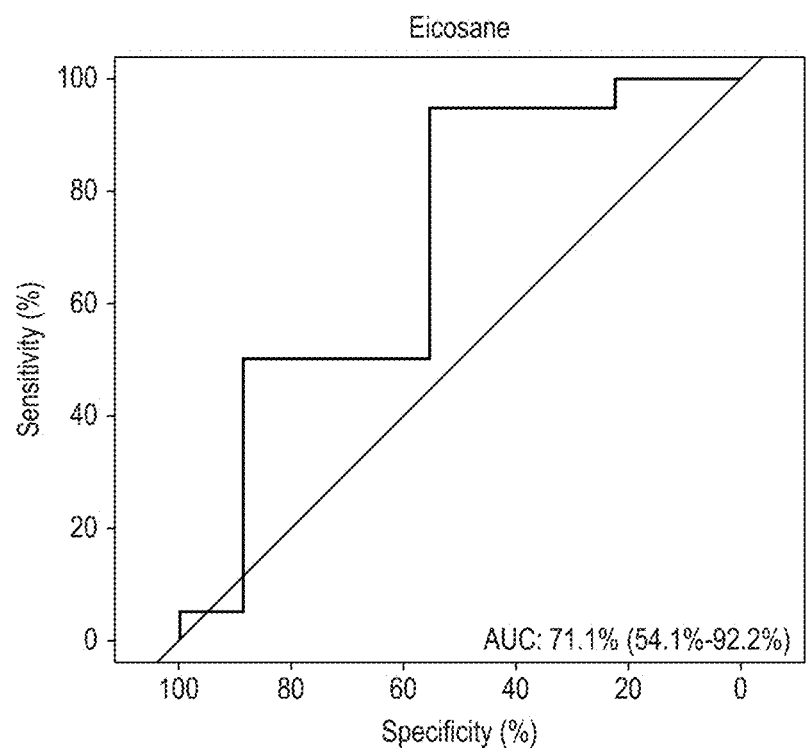
FIG. 2A(iii)
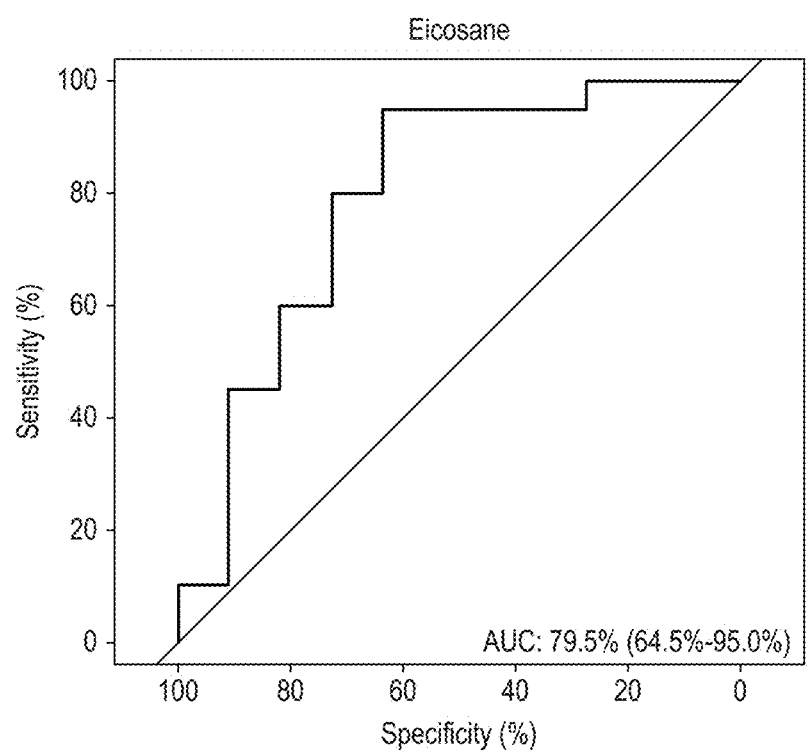
FIG. 2A(iv)

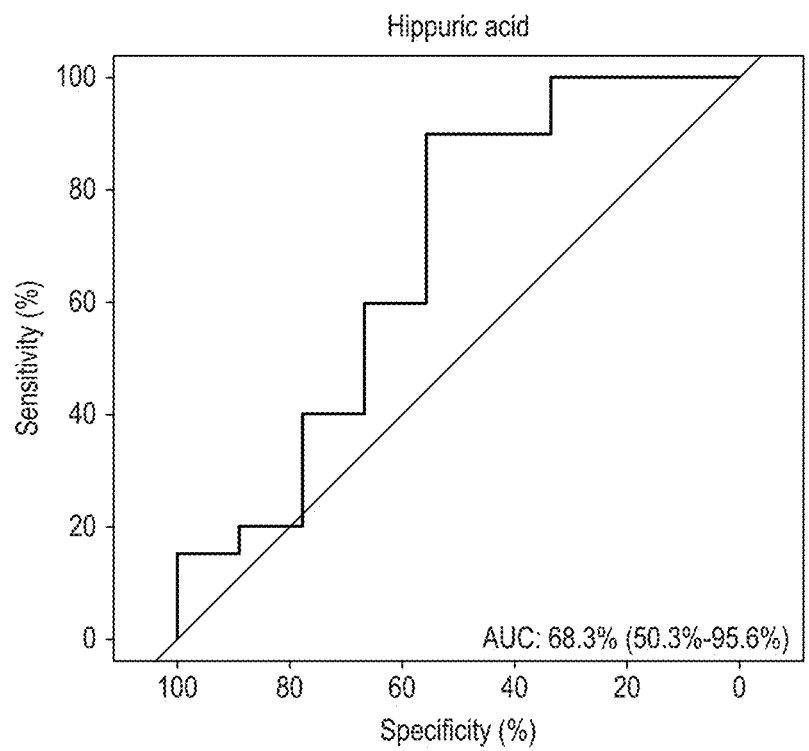
FIG. 2A(v)
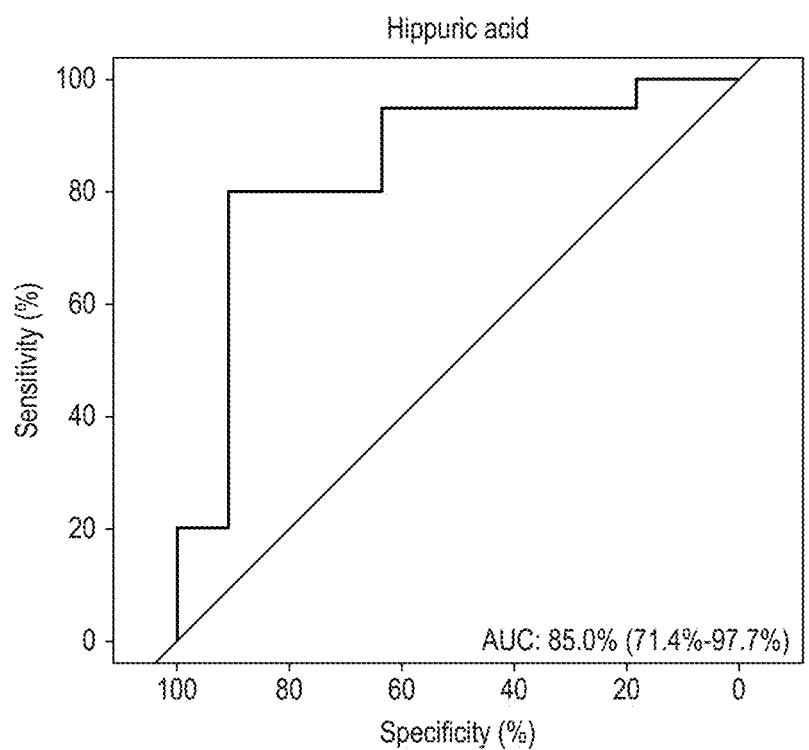
FIG. 2A(vi)

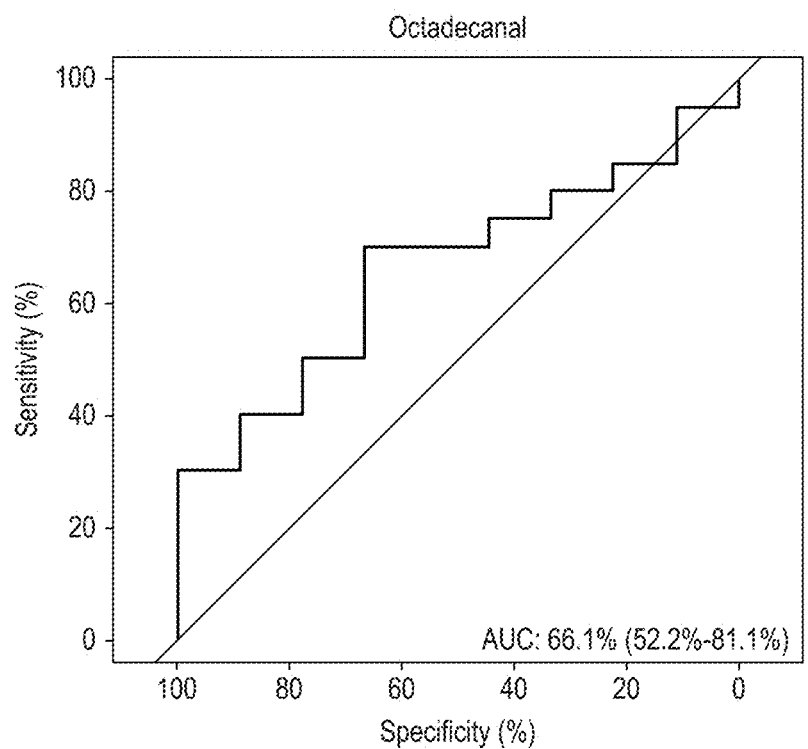
FIG. 2A(vii)
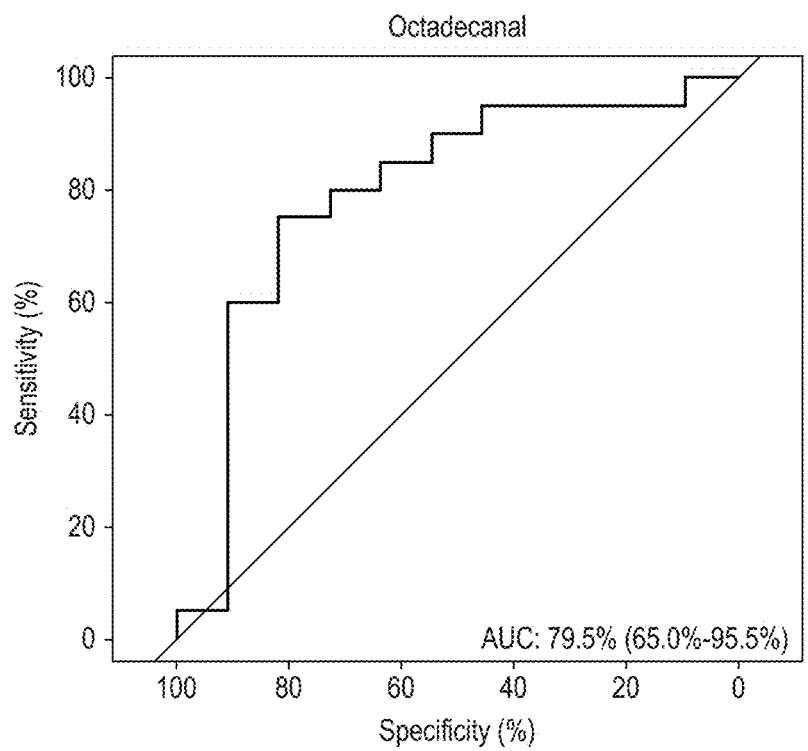
FIG. 2A(viii)

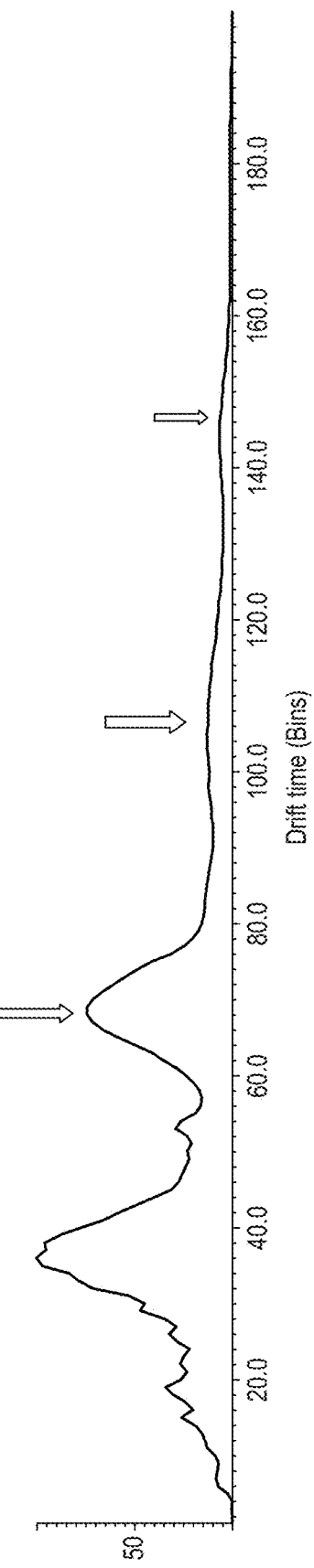
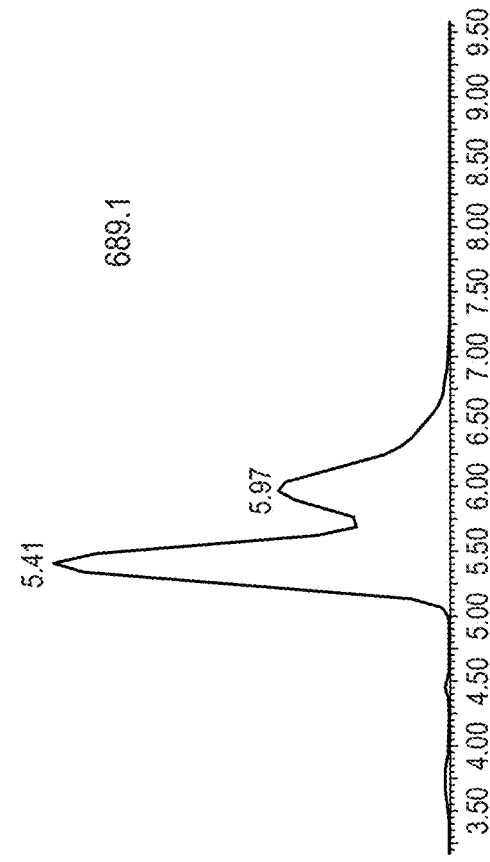
FIG. 18A
FIG. 18B

BIOMARKERS AND USES THEREOF

CROSS-REFERENCE TO RELATED APPLICATIONS

This is a National Stage Entry under 35 U.S.C. 371 of International Patent Application No. PCT/GB2019/052169, filed Aug. 1, 2019, which claims priority to UK Patent Application No. GB1812561.7, filed Aug. 1, 2018. These applications are incorporated by reference herein.

TECHNICAL FIELD OF THE INVENTION

The present invention relates to methods and devices for analysing sebum, and in particular for assessing whether an individual has Parkinson's Disease (PD).

BACKGROUND TO THE INVENTION

Parkinson's disease (PD) is a progressive, neurodegenerative disease, the diagnosis of which, at present, is informed by observation and measurement of clinical symptoms. The most important clinical symptom of PD is a reduction in the speed and amplitude of movement. Other symptoms including stiffness and tremor are also common [1]. There is an exigent need to detect PD before manifestation of such clinical symptoms as these are predominantly observable only once the disease has progressed to a stage when more than 60% of the dopaminergic neurons in the substantia nigra are lost [2].

More than 1 in 40 people will develop Parkinson's disease (PD) at some point in their life. The symptoms of PD worsen as the disease progresses, and since the majority of these symptoms are only detected once the neurodegenerative process is already well advanced, there is little opportunity for early interventions. This is also attributable to a limited understanding of the causation of PD at the molecular level coupled with clinical variations in signs and symptoms that occur in the early stages of PD [4].

Early pilot studies with a 'Super Smeller' have indicated that a distinct musky odour was associated with the sebum from PD subjects [3]. This Super Smeller has demonstrated a unique ability to detect PD by odor [2]. They have an extremely sensitive sense of smell, and this enables them to detect and discriminate odors not normally detected by those of average olfactory ability. Preliminary tests with t-shirts and medical gauze indicated the odor was present in areas of high sebum production, namely the upper back and forehead, and not present in armpits, that are more commonly associated with human odor [2]. Over-production of sebum, seborrhoea, is a known non-motor symptom of PD [5], and Parkinson's skin has recently been shown to contain phosphorylated α-synuclein, a molecular hallmark of PD [6]. Identification and quantification of the metabolites that are associated with this distinctive PD odor could enable rapid, early screening of PD as well as provide insights into molecular changes that occur at disease onset and enable stratification of the disease in future.

Volatile organic compounds (VOCs) generally are associated with characteristic odors, although some volatiles may also be odorless [7]. Volatilome (volatile metabolites) analysis using mass spectrometry has been used for medical diagnostics [8-12] as well as for analysis of the quality of food such as oils and honey [13-15], beverages and in the health and beauty industry [17]. TD-GC-MS has been used as a volatilome analysis platform for the detection of bacteria implicated in ventilator associated pneumonia [11], for differentiation between human and animal decomposition [18], for characterisation of exhaustion profile of activated carbon as well as aerosol detection from e-cigarettes [20].

It is an object of the present invention to address one or more problems associated with identification of PD. It is also an object of the present invention to provide a new method of diagnosing and/or identifying those individuals who may be suffering from, or have an early onset of, PD. It would be preferred if a method of diagnosis could be provided, which is non-invasive and which can be performed by a range of healthcare professionals or carers.

SUMMARY OF INVENTION

In accordance with a first aspect of the present invention, there is provided a method of assessing whether an individual has Parkinson's Disease (PD) and/or is no longer responding to treatment, the method comprising the identification of one or more volatile compounds in the sebum of the individual.

In accordance with a related aspect of the present invention, there is provided a method of diagnosing Parkinson's Disease in an individual, or diagnosing that a current treatment is not effective or no longer effective in the treatment of Parkinson's Disease, the method comprising the identification of one or more volatile compounds in the sebum of the individual.

In accordance with a yet further related aspect of the present invention, there is provided one or more biomarkers for use in the diagnosis of Parkinson's Disease, wherein the biomarkers comprise the isolation and/or identification of one or more volatile compounds in the sebum of the individual.

In accordance with another related aspect of the present invention, there is provided a method of identifying and treating an individual who is suffering from Parkinson's Disease (PD), the method comprising: analyzing the sebum of the individual for the presence of one or more volatile compounds, and if the presence of one or more volatile compounds is found, administering a therapeutically effective amount of a neuroprotective agent to the individual.

In accordance with another aspect of the present invention, there is provided a method of treating an individual with a neuroprotective agent so as to delay the onset or progression of Parkinson's Disease, the method comprising:
  determining if one or more volatile compounds are in the sebum of the individual; and
  administering to the individual a therapeutically effective quantity of a neuroprotective agent.

The Parkinson's Disease may be early, mid or late onset.

There is a general prejudice in the art against using sebum as a biofluid for diagnostics due to the non-sterile environment of the skin and potential contaminants (such as soaps) which may be present and affect test results. However, the inventors have advantageously and unexpectedly found that molecules present on skin surface can be used to distinguish individuals having Parkinson's Disease from a Control subject. Using a sebum sample to assess the Parkinson's Disease status of an individual is advantageous for a number of reasons. Firstly, collecting sebum is a non-invasive method. Secondly, it should be possible to directly sample, and analyse sebum without preparation and extraction of metabolites from sebum and therefore provide opportunities to develop a rapid screening/diagnostic test for Parkinson's Disease. Such tests could be utilised as a companion diagnostic alongside the treatment with neuroprotective agents so as to delay the onset of Parkinson's Disease or attenuate its progression in an individual. Parkinson's Disease affects an ageing population globally and a diagnostic test that is non-invasive would be well received by numerous public and private healthcare providers across the globe.

In certain preferred embodiments, the method comprises the identification that one or more of the volatile compounds are elevated or reduced with reference to a control sebum value. It will be apparent to the skilled addressee that the control sebum value would typically be the value in a healthy individual or an individual who is deemed not to be suffering from Parkinson's Disease. Alternatively, the control sebum value could be the value of the individual when they are responding to a therapy as often individuals initially respond well to treatment, but then need to have their doses increased or their therapies switched to a different therapeutic over time as the disease progresses.

The one or more differentiated compounds present in sebum may comprise at least one or more lipids, cardiolipins, phosopholipids, glycerophospholipids glycolipids, sphingolipids, ceramides, sphingomyelin, fatty acids, waxy esters.

The one or more volatile compounds may comprise one or more selected from the following: dodecane, eicosane, octacosane, hippuric acid, octadecanal, artemisinic acid, perillic aldehyde (also known as Perillaldehyde, or *perilla* aldehyde), diglycerol, hexyl acetate, 3-hydroxytetradecanoic acid and/or octanal.

In certain preferred embodiments the method comprises the identification that one or more of the following as occurred: perillic aldehyde is reduced; hippuric acid is elevated; eicosane is elevated; and/or octadecanal is elevated.

The term, "volatile compound" is intended to mean a compound which easily becomes a vapor or gas when isolated and/or subjected to mass spectrometry.

The method may be used for assessing whether an individual has early onset Parkinson's Disease (PD) which is often very difficult to assess. The method may also be used for assessing (or continually assessing) individuals who have a hereditary and/or environmental risk of developing Parkinson's Disease.

Unexpectedly, the inventors have found that not all typical solvents are suitable in the extraction of volatile compounds from sebum. It has been identified that the volatile compounds in the sebum are best extracted using methanol.

It will be apparent to the skilled addressee that a number of methods for identifying and/or quantifying the sebum based compounds may be employed.

Generally, mass spectrometry (MS) may be used to detect, identify and/or quantify analytes (such as volatile compounds) in complex matrices, such as biological samples, usually as part of a hyphenated technique, for example liquid chromatography (LC)—MS or gas chromatography (GC)—MS. As such, conventional MS ionization sources such as electrospray (ES) and chemical ionization (CI), respectively, are suitable. Other ionization sources are known.

If MS is used for identifying and/or quantifying the sebum based compounds, preferably, it is used to identify compounds in the significantly higher molecular mass region of >800 m/z, >1000 m/z, or >1200 m/z. Typically, biofluids (such as blood and urine) assess compounds in the lower molecular mass region of ≤1000 m/z. The present inventors have surprisingly for the first time, shown that sebum can be used as a sampling biofluid for PSI-MS and that it enables the detection of skin surface molecules with a significantly higher molecular mass of >800 m/z. Ion mobility-mass spectrometry (IM-MS) was also employed by the inventors to further evaluate these high molecular weight metabolites and the mass spectra of human sebum surprisingly showed the presence of four envelopes at the higher mass region (m/z 800-2500) consisting of singly charged peaks.

For routine clinical laboratories and point of care applications, for example, there is a desire to reduce sample pre-treatment and/or simplify analysis and/or data interpretation. Hence, ambient ionization sources may be preferred, for example desorption electrospray ionization (DESI), direct analysis in real time (DART), atmospheric solids analysis probe (ASAP) and paper spray (PS).

Paper spray is a direct sampling ionization method for mass spectrometry, including of complex mixtures. A sample, for example 0.4 μL, is loaded onto a triangular piece of paper and wetted with a solvent, for example 10 μL of methanol: water. Ions from the sample are generated by applying a high voltage, for example 3-5 kV DC or 4 to 6 kV DC, to the paper. By directing the ions generated at the apex of the paper towards an inlet of a mass spectrometer, mass spectrometry thereof may be performed.

In one example, the mass spectrometry is performed using a mass spectrometer comprising an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) an Atmospheric Solids Analysis Probe ("ASAP") ion source; (xxviii) a Laser Ablation Electrospray Ionisation ("LAESI") ion source; (xxix) a Desorption atmospheric pressure photoionization ("DAPPI") ion source; (xxx) paper spray ("PS"). Paper spray is preferred.

The present inventors have advantageously demonstrated the versatility of thermal desorption-gas chromatography mass spectrometry (TD-GC-MS) as a tool for studying volatile compounds, and its applicability to identifying the metabolites that cause the distinct scent of PD in sebum.

In the alternative, identification may be by means of an immunoassay.

The sebum may be collected and stored in a number of ways. For example, the sebum may be collected by swabbing the back of an individual with a medical gauze, absorbent paper or cotton wool. Alternatively, the sebum may be scraped off the back of an individual using a rigid implement such as a spatula and then deposited in a collection tube or other device. Generally speaking, the sebum is relatively stable at ambient temperatures so no further treatment of the sebum is necessary before the extraction of the volatile compounds. However, if desired, the sebum may be mixed with a suitable preserver or buffer before extraction.

In certain embodiments, there is provided a smart paper envelope that can be used to collect sebum sample, non-invasively and posted back to a laboratory which can then directly analyse sample off the paper using very small amount of extraction solvents and provide the results shortly thereafter.

In accordance with a further aspect of the present invention, there is provided a method of extracting target analytes from sebum comprising:
(a) contacting the sebum with methanol so as to form a mixture.

The method may further comprise:
(b) shaking and/or vortexing the mixture, and further optionally, sonicating the mixture.

The method may further comprise:
(c) optionally splitting the mixture into two fractions.

The method may further comprise drying the mixture. The mixture may be dried by means of a vacuum concentrator such as a SpeedVac Concentrator.

The sebum may be on any number of different substrates, such as any textile cellulose medium or fabric or artificial surface. Preferably, the sebum may be on a cotton swab, gauze, wood or cellulose based paper.

The target analytes may comprise one or more volatile compounds, such as one or more selected from the following: dodecane, eicosane, octacosane, hippuric acid, octadecanal or dodecane, artemisinic acid, perillic aldehyde or diglycerol, hexyl acetate or dodecane, and 3-hydroxytetradecanoic acid or octanal. Or of the class of compounds found in sebum comprising one or more selected from lipids, cardiolipins, phosopholipids, glycerophospholipids glycolipids, sphingolipids, ceramides, sphingomyelin, fatty acids, waxy esters.

It is preferred that the method is used for assessing whether an individual has a disease, such as Parkinson's Disease (PD).

The extracted target analytes may be for subsequent analysis by mass spectrometry.

In accordance with another aspect of the present invention, there is provided an assay device for detecting presence of a target analyte in sebum by mass spectrometry, the device comprising:
a first layer comprising a wicking and/or a porous material for absorbing and/or collecting the sebum thereon and extraction of the target analyte therefrom; and
a second layer comprising an impermeable material arrangeable over the first layer;
wherein the device is arrangeable to provide an emitter for paper spray mass spectrometry.

In accordance with yet a further aspect of the present invention, there is provided a method of detecting presence of a target analyte in sebum using an assay device as described above comprising:
providing the sebum on the first layer, for example by contacting a patient therewith;
arranging the second layer over the first layer, thereby covering the sebum thereon;
extracting the target analyte, if present, from the sebum by exposing the sebum to a solvent comprising methanol;
providing an emitter for paper spray mass spectrometry from the first layer; and
performing mass spectrometry using the provided emitter, thereby detecting the extracted, target analyte.

In accordance with yet a further aspect of the present invention, there is provided a method of extracting a target analyte, from sebum, for mass spectrometry thereof, the method comprising:
exposing the sebum to a solvent comprising methanol;
optionally, wherein the exposing is at a temperature in a range from −10° C. to +10° C., preferably in a range from −5° C. to +5° C., more preferably in a range from 0° C. to 3° C.; and
optionally, sonicating the exposed sebum.

In a yet further aspect of the present invention, there is provided a method of detecting presence of a target analyte in sebum, comprising:
extracting the target analyte, if present, from the sebum as herein above described;
performing mass spectrometry, optionally liquid chromatography-mass spectrometry, on the extracted target analyte, thereby detecting the target analyte, if present.

A number of neuroprotective agents may be used in combination with the methods described above. For example, Roche/Prothena is developing a neuroprotective agent denoted "PRX-002" which is a monoclonal antibody targeting alpha-synuclein. Clinical trials have been conducted for PRX-002 at a dosing of 0.3 mg/kg, 1.0 mg/kg, 3.0 mg/kg, 10 mg/kg, 30 mg/kg, or 60 mg/kg where participants received 3 intravenous infusions every 4 weeks of PRX002 or placebo and were monitored during a 24-week observational period. PRX-002 could be administered to an individual who has been determined as having Parkinson's Disease by the methods of the present invention.

Features, integers, characteristics, compounds, methods, assays and devices described in conjunction with a particular aspect, embodiment or example of the invention are to be understood to be applicable to any other aspect, embodiment or example described herein unless incompatible therewith. All of the features disclosed in this specification (including any accompanying claims, abstract and figures), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

DETAILED DESCRIPTION OF THE INVENTION

Aspects and embodiments of the present invention will now be illustrated, by way of example, with reference to the accompanying figures. Further aspects and embodiments will be apparent to those skilled in the art. All documents mentioned in this text are incorporated herein by reference.

FIG. 1 shows the PLS-DA classification model (A.) PLS-DA predictions showing 90% correct prediction of Parkinson's sample classifications with validation using 5-fold cross validation. (B.) PLS-DA modelling was further tested using permutation tests (where the output classification was randomised; n=26) and results are plotted as a histogram which shows frequency distribution of correct classification rate (CCR) which yielded CCRs ranging between 0.4 to 0.9 for permutated models. The observed model was significantly better than most of the permuted models (p<0.1); shown by arrow;

FIG. 2 shows ROC curves, box plots and AUC comparison for analytes of interest (A.) ROC curves for both discovery ((i), (iii), (v) and (vii)) and validation ((ii), (iv), (vi) and (viii)) cohort for four analytes common to both experiments. Numbers in parenthesis are confidence intervals calculated computed with 2000 stratified bootstrap replicates and grey line represents random guess. (B.) Box plot for both discovery and validation cohort for four analytes in common, comparing the means on log scaled peak areas of these analytes. (C.) AUC comparison between analytes;

FIG. 3 shows olfactograms from control and PD gauzes GC-MS chromatogram from three drug naïve Parkinson's subjects and a blank gauze overlaid by red shaded area shows overlap between real time GC-MS analysis and smell using odor port. Figure shows retention time between 10 and 21 min where the Super-Smeller had described odors linked to various peaks. The highlighted area between 19.2 and 21 minutes (enlarged on right) is of particular interest as 3 out of 4 compounds overlap with odor port results, where the Super-Smeller described the scent of PD to be very strong. The peaks are not seen in a blank gauze at the same time window as shown by normalised relative peak intensities to the highest peak in each chromatogram;

FIG. 4 shows ROC plots. (A.) ROC plot generated using combined samples from both cohorts and all five metabolites that were common and differential between control and PD. The shaded area indicates 95% confidence intervals calculated by Monte Carlo Cross Validation (MCCV) using balanced sub-sampling with multiple repeats. (B.) ROC plots generated using all nine metabolites that were common between the two cohorts (but not necessarily differential using Student's t-test or expressed in the same direction between cohorts). Each model was built using PLS-DA to rank all variables and top two important variables were selected to start with. Then in each subsequent model additional variables by rank were added to generate ROC curve. Confidence intervals were calculated by Monte Carlo Cross Validation (MCCV) using balanced sub-sampling with multiple repeats.

Figure 14:
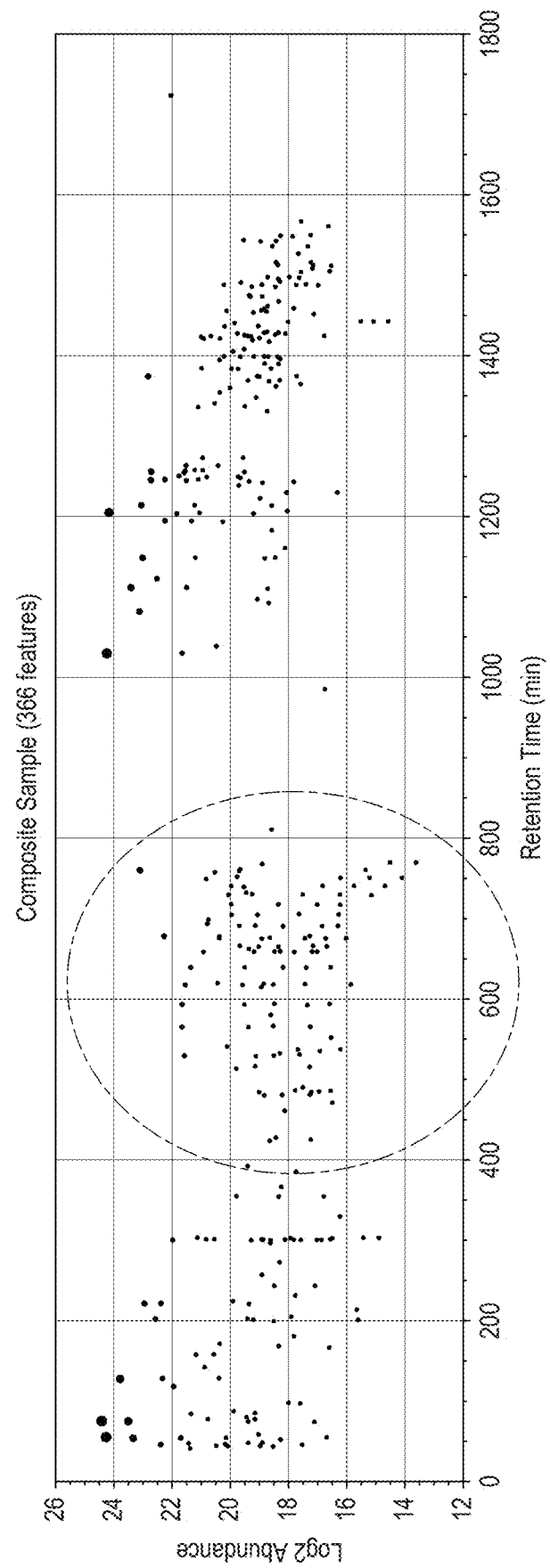
Figure 15A:
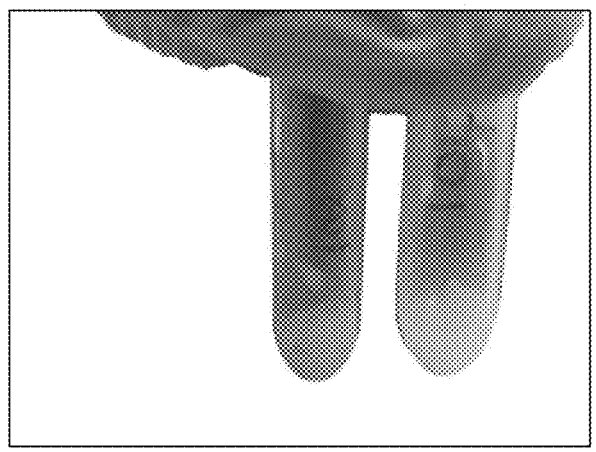
Figure 15B:
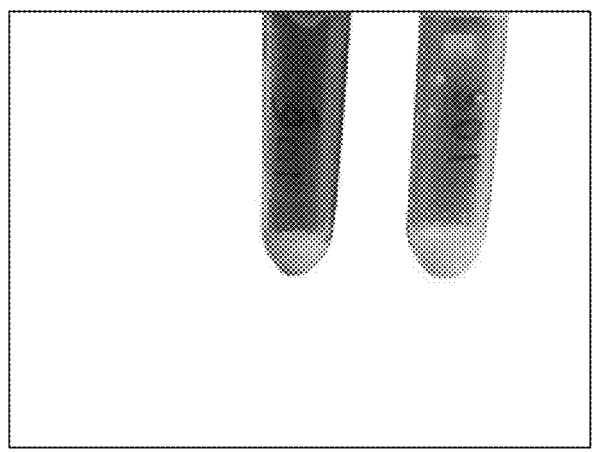
Figure 15C:
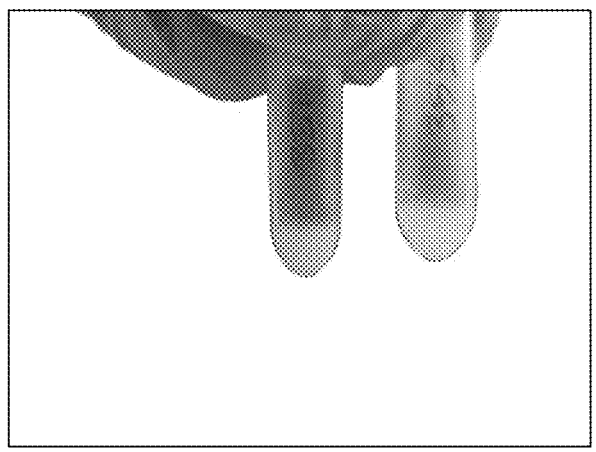
Figure 16:
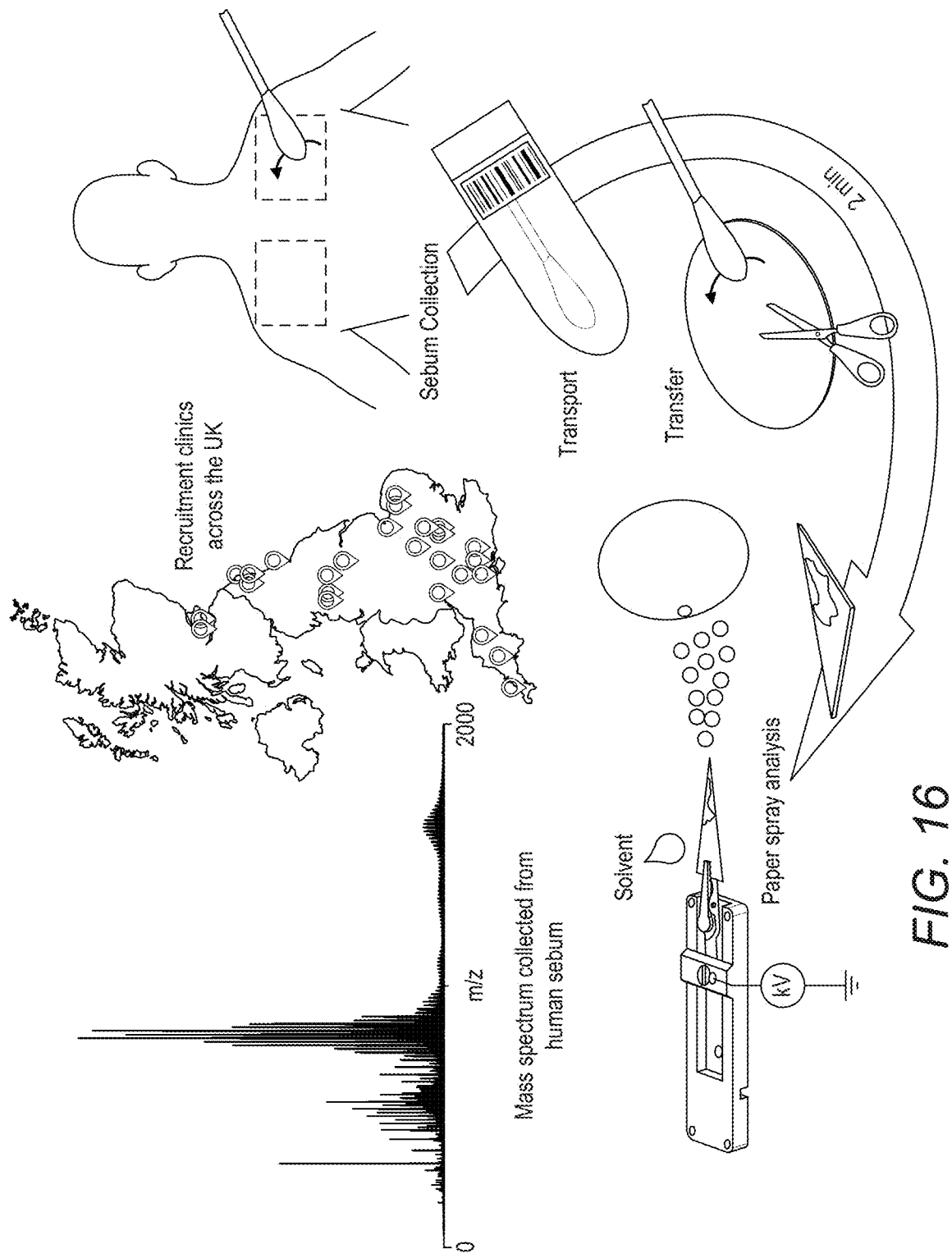
Figures 17A, 17B:
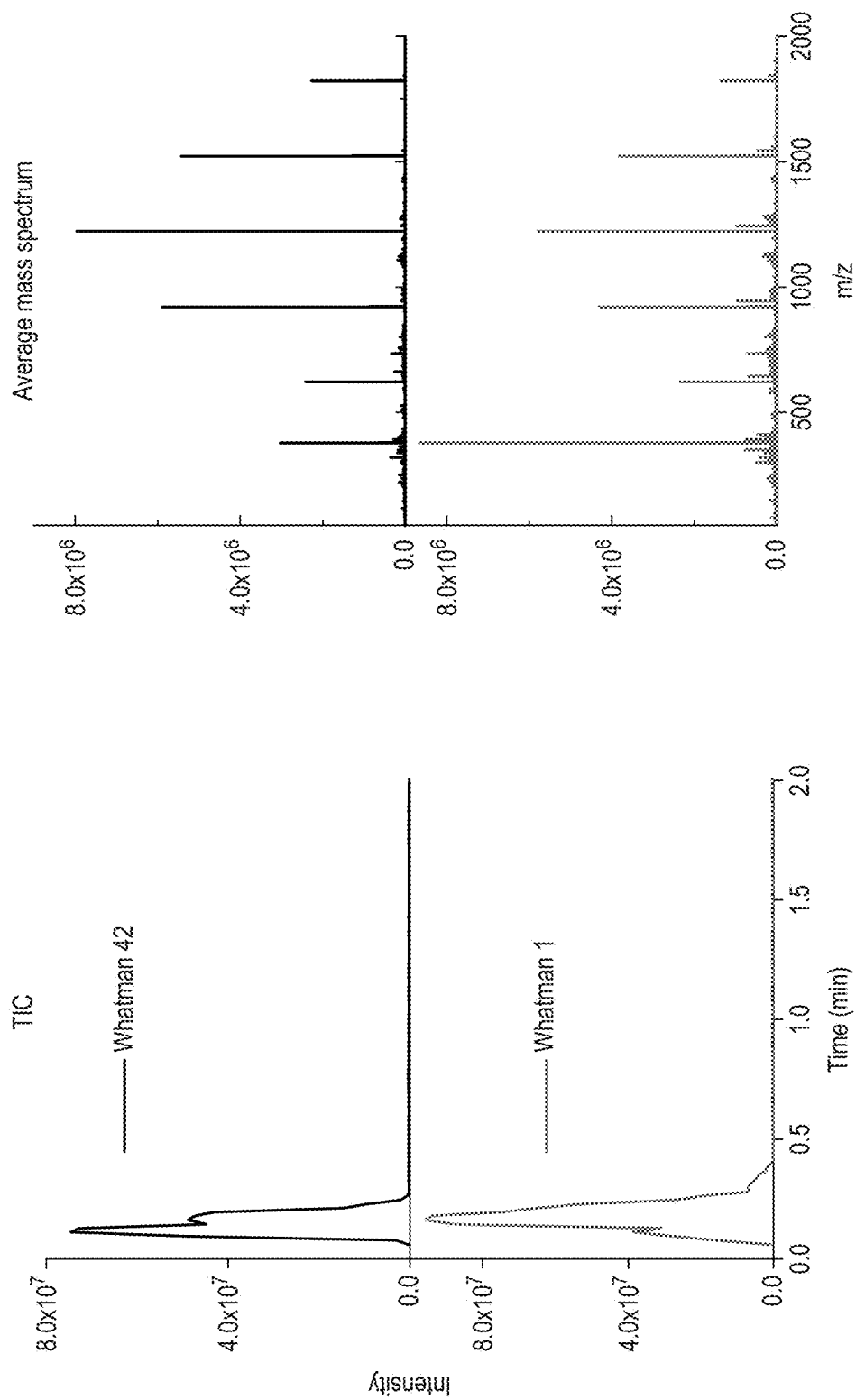
Figure 19:
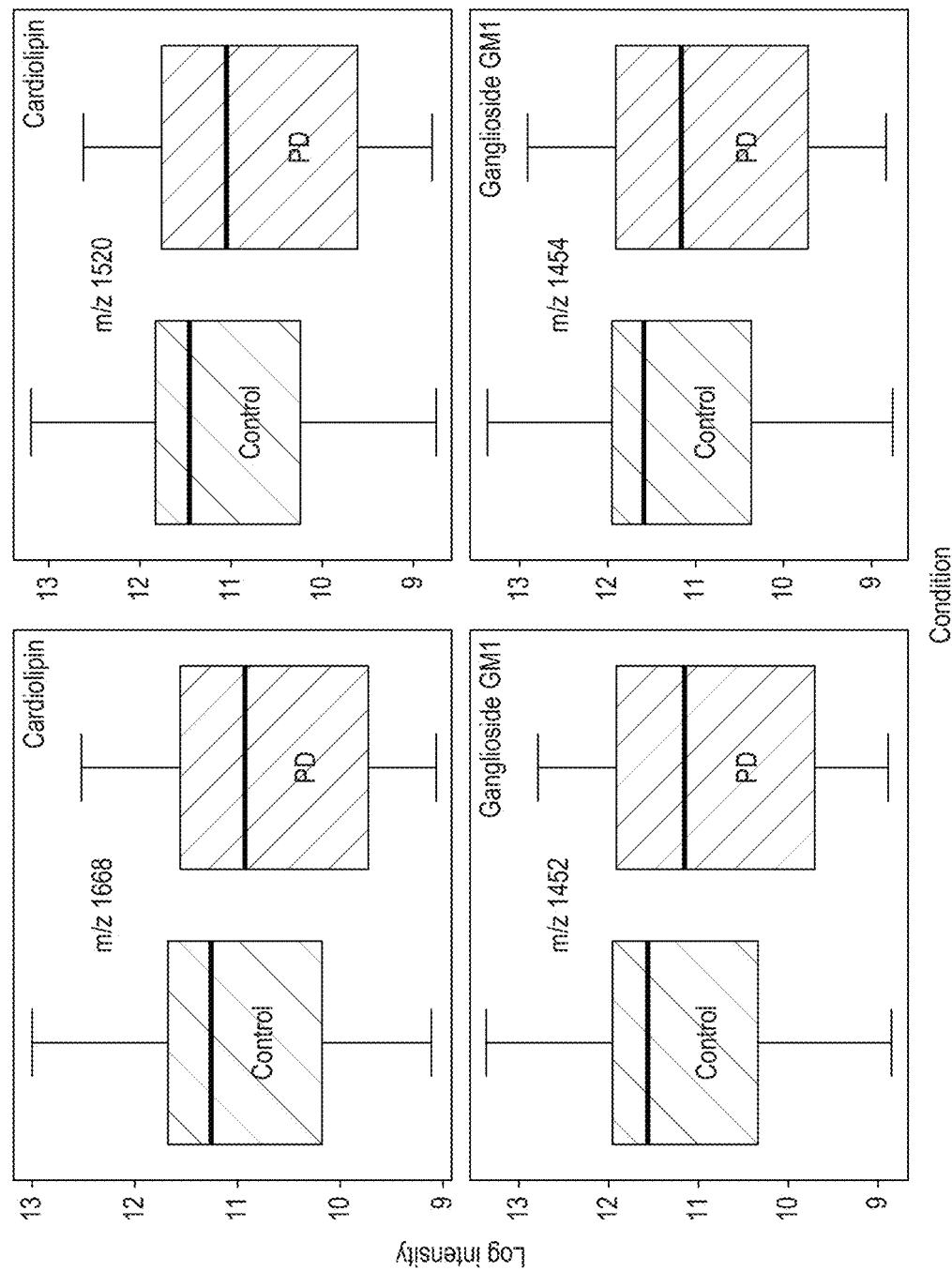
Figure 20:
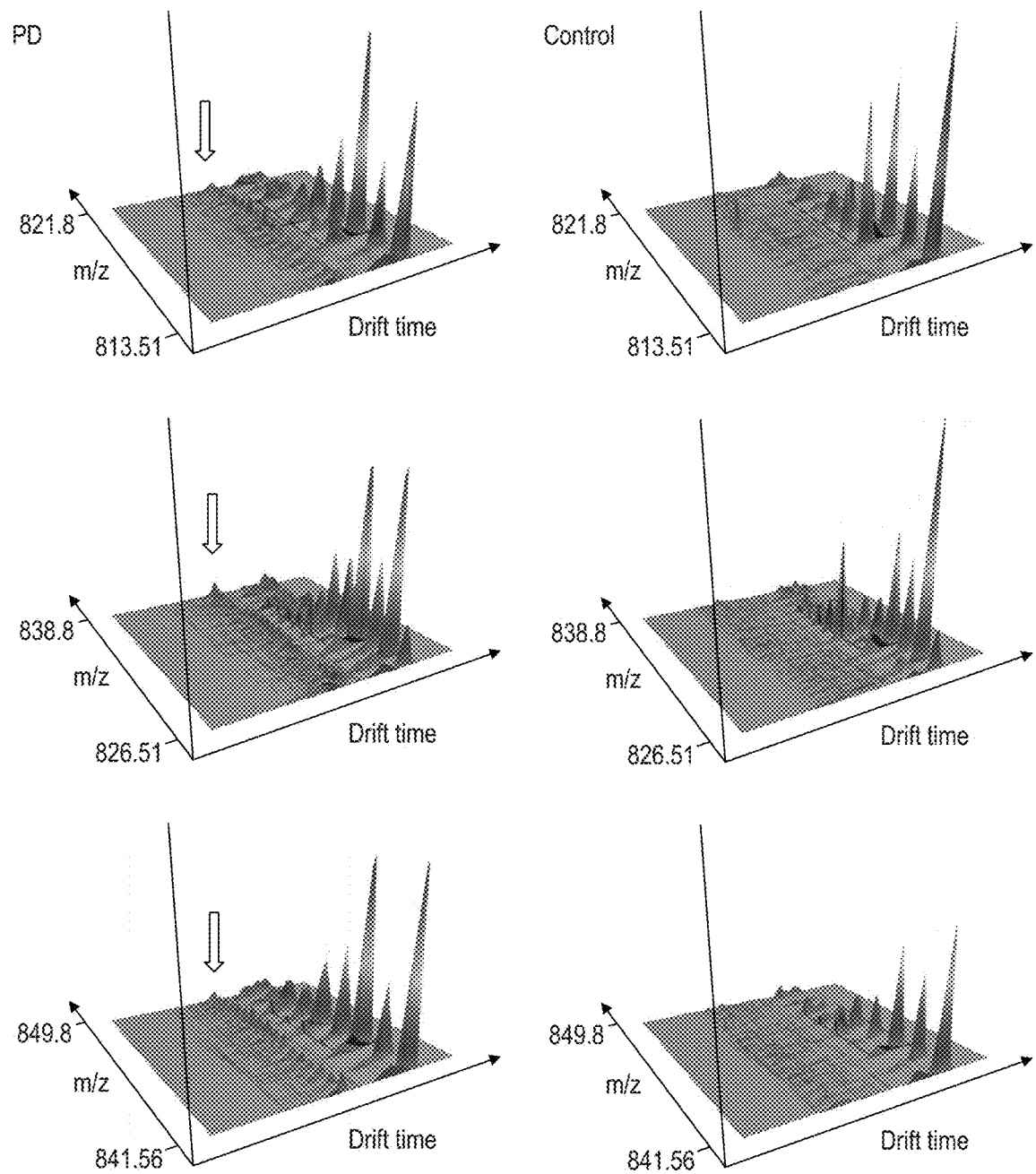
Figure 20:
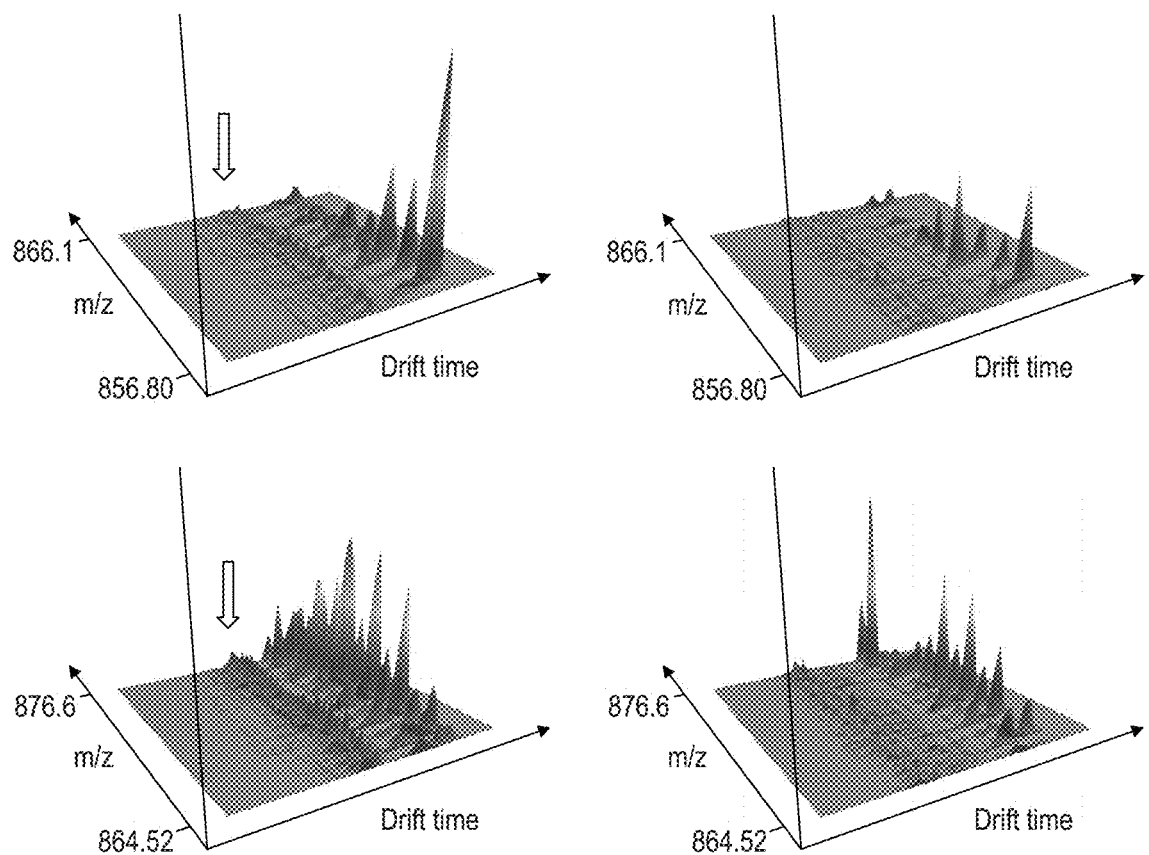

FIG. 14 shows a plot of the number of features higher in samples in the PEG area; and FIG. 15 shows photographs of vials demonstrating the results of the extraction protocol optimisation in Example 3. (A). Gauze extraction using Toluene paired to a Toluene:Methanol (20:80) reconstitution shows the formation of a solid residue—the addition of chloroform followed by centrifugation (x2 steps) allowed a clear supernatant to be obtained. (B.) Toluene gauze extraction followed by a Toluene:Methanol (50:50) reconstitution shows a solid substance has formed. (C.) Folch extraction (Methanol:Water:Chloroform) of the gauze swab and subsequent reconstitution of the separated chloroform layer shows a cloudy solution has formed which did not reconstitute back in Water:Methanol (80:20)—stages of chloroform addition followed by sonication and centrifugation improved reconstitution results however too much sample was lost in the process;

FIG. 16 shows a schematic representation of PSI-MS analysis of human sebum and a mass spectrum recorded from it;

FIG. 17 shows a comparison of PSI-MS data recorded from Whatman 42 and 1 (A) as a total ion chromatogram and (B) as an average mass spectrum;

FIG. 18 shows (A) a total ion chromatogram recorded from human sebum showing arrival time distribution of different diagnostic ions, (B) arrival time distribution of a single ion indicating the presence of isomeric structures and (C) a drift time vs m/z plot. The red dots represent equal m/z values. The zoomed image inset indicates the presence of a species with the same mass but with a different drift time;

FIG. 19 shows box plots for four m/z values that are statistically important with a p-value of <0.1; and FIG. 20 shows m/z vs drift time plots for the m/z values presented in Table 7 showing the separation of these ions on a drift time scale in PD samples. No separation was observed in the control samples.

EXAMPLE 1—EXPERIMENTS TO ASSESS SEBUM FOR THE PRESENCE OF VOLATILE BIOMARKERS FOR PARKINSON'S DISEASE

Study Participants

The participants for the study were part of a nationwide recruitment process taking place at 25 different NHS clinics. The participants were selected at random from these sites. The study was performed in three stages. The first two stages (discovery and validation) consisted of 30 samples (a mixture of control, PD participants on medication and drug naïve PD subjects as shown in Table 1 below).

TABLE 1

Details of the collecting sites in the UK.

| | SITE |
|---|---|
| 1 | Addenbrooks (Cambridge) |
| 2 | Bournemouth |
| 3 | Cornwall/Truro |
| 4 | Lothian-Western General Edinburgh |
| 5 | Edinburgh-MRC/Regenerative Med (Royal Infirmary of Edinburgh) |
| 6 | Edinburgh-Primary Care NHS Lothian (Seb Derm) |
| 7 | Hampshire |
| 8 | Nottingham |
| 9 | Pennine |
| 10 | Salford |
| 11 | Salisbury |
| 12 | Sheffield |
| 13 | South Tees |
| 14 | Southern Health |
| 15 | Luton & Dunstable |
| 16 | Portsmouth |
| 17 | Northumbria |
| 18 | London North West |
| 19 | Bath |
| 20 | Gateshead |
| 21 | Sunderland |
| 22 | Plymouth |
| 23 | Newcastle Upon Tyne Hospitals NHS Foundation Trust (Newcastle University) |
| 24 | Royal Devon and Exeter NHS Foundation Trust |
| 25 | Imperial College Healthcare NHS Trust |

The first cohort was used for volatilome discovery, and the second cohort was used to validate the significant features discovered in first cohort. A third cohort consisting of three drug naïve PD participants was used for smell analysis from the Super Smeller. The metadata analysis for these participants is shown in Table 2 below.

TABLE 2

Participant numbers and metadata per wave.

| | Wave 1 (untargeted profiling) | | | |
|---|---|---|---|---|
| | Control (n = 10) | Drug Naïve PD (n = 10) | PD on medication (n = 10) | p-value |
| Age (years) | 64.8 ± 3.06 | 72.82 ± 8.42 | 64.67 ± 2.55 | 0.01* |
| BMI | 27.10 ± 3.50 | 26.94 ± 4.08 | 25.33 ± 3.44 | 0.64 |

TABLE 2-continued

Participant numbers and metadata per wave.

| | | | | |
|---|---|---|---|---|
| Gender (M/F ratio) | 0.84 | 1.20 | 0.80 | 0.88 |
| Alcohol intake (yes/no ratio) | 4.5 | 0.37 | 2 | 0.03* |
| Smoker | 1 | 0 | 0 | 0.39 |

Wave 2 (targeted discovery)

| | Control (n = 11) | Drug Naïve PD (n = 11) | PD on medication (n = 9) | p-value |
|---|---|---|---|---|
| Age (years) | 55.78 ± 18.87 | 75.40 ± 6.85 | 68.90 ± 11.76 | 0.02* |
| BMI | 28.96 ± 11.01 | 25.74 ± 3.83 | 24.98 ± 3.54 | 1.00 |
| Gender (M/F ratio) | 0.26 | 1.50 | 1 | 0.10 |
| Alcohol intake (yes/no ratio) | 0.8 | 9 | 1.5 | 0.10 |
| Smoker | 0 | 0 | 1 | 0.24 |

Wave 3 (odour port validation, drug naïve PD subjects only, n = 3)

| | |
|---|---|
| Age (years) | 65.66 ± 3.30 |
| BMI | 23.46 ± 1.80 |
| Gender (M/F ratio) | 2 |
| Alcohol intake (yes/no ratio) | 2 |
| Smoker | 0 |

(*indicates significant difference between controls, drug naïve and PD with medication groups)

Figure 4A:
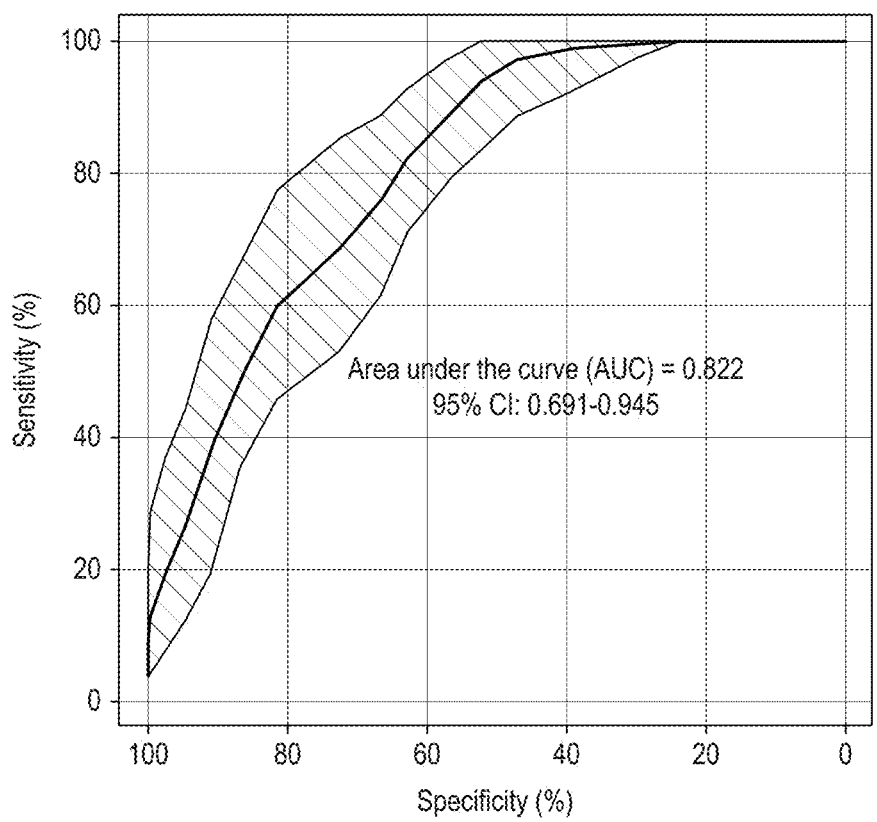
Figure 4B:
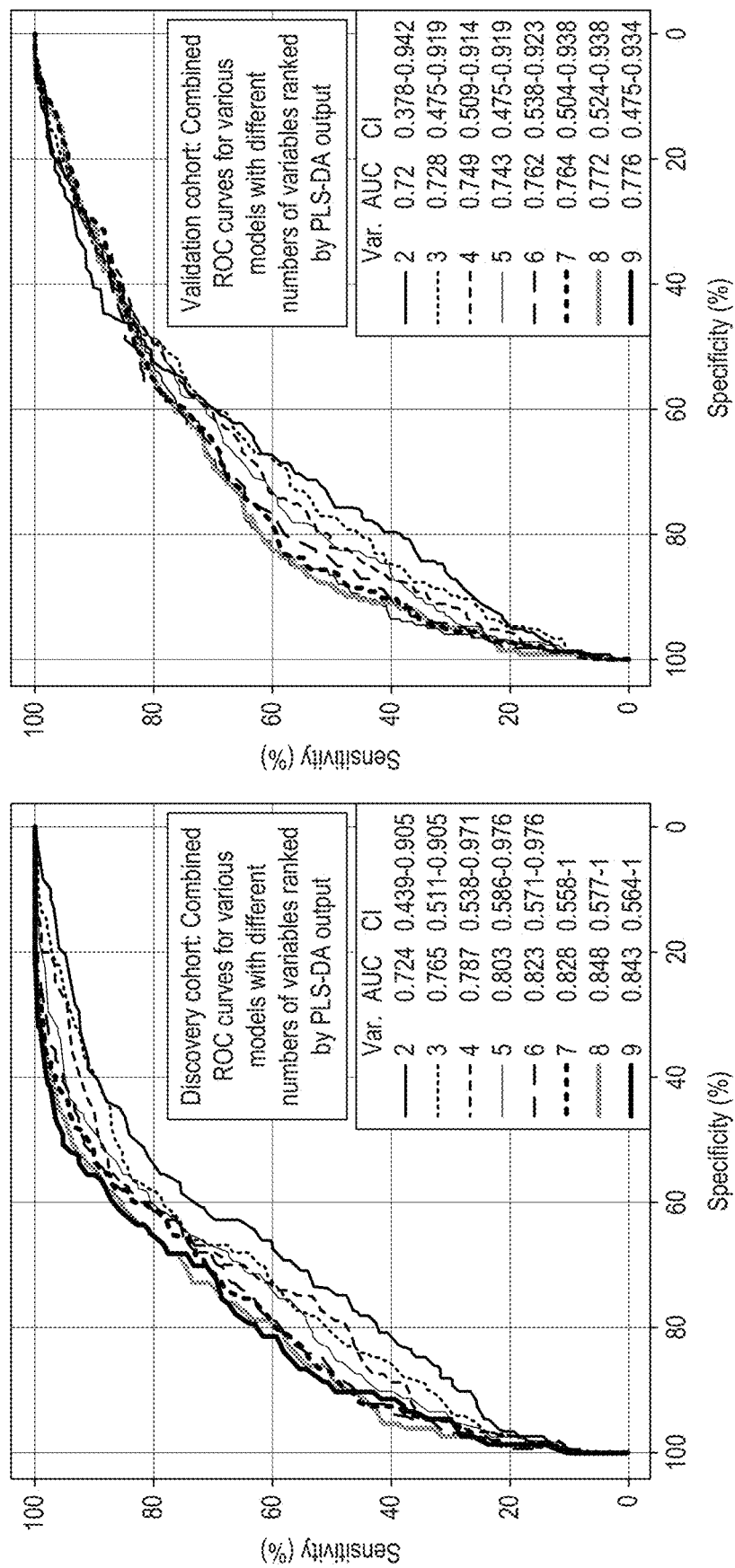
Figure 5:
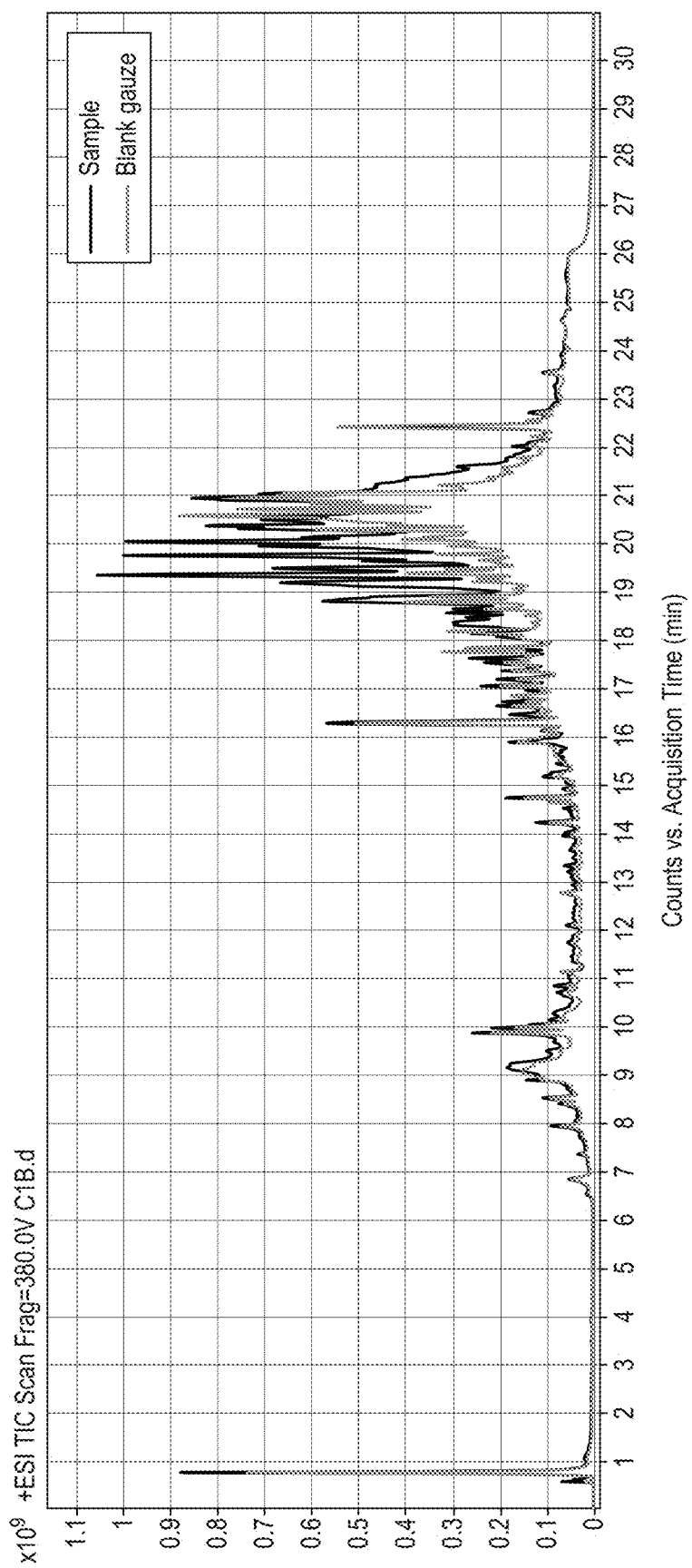
FIG. 5 shows a plot of blank gauze vs sample reconstituted in $H_2O$:ACN (50:50)
Figure 6:
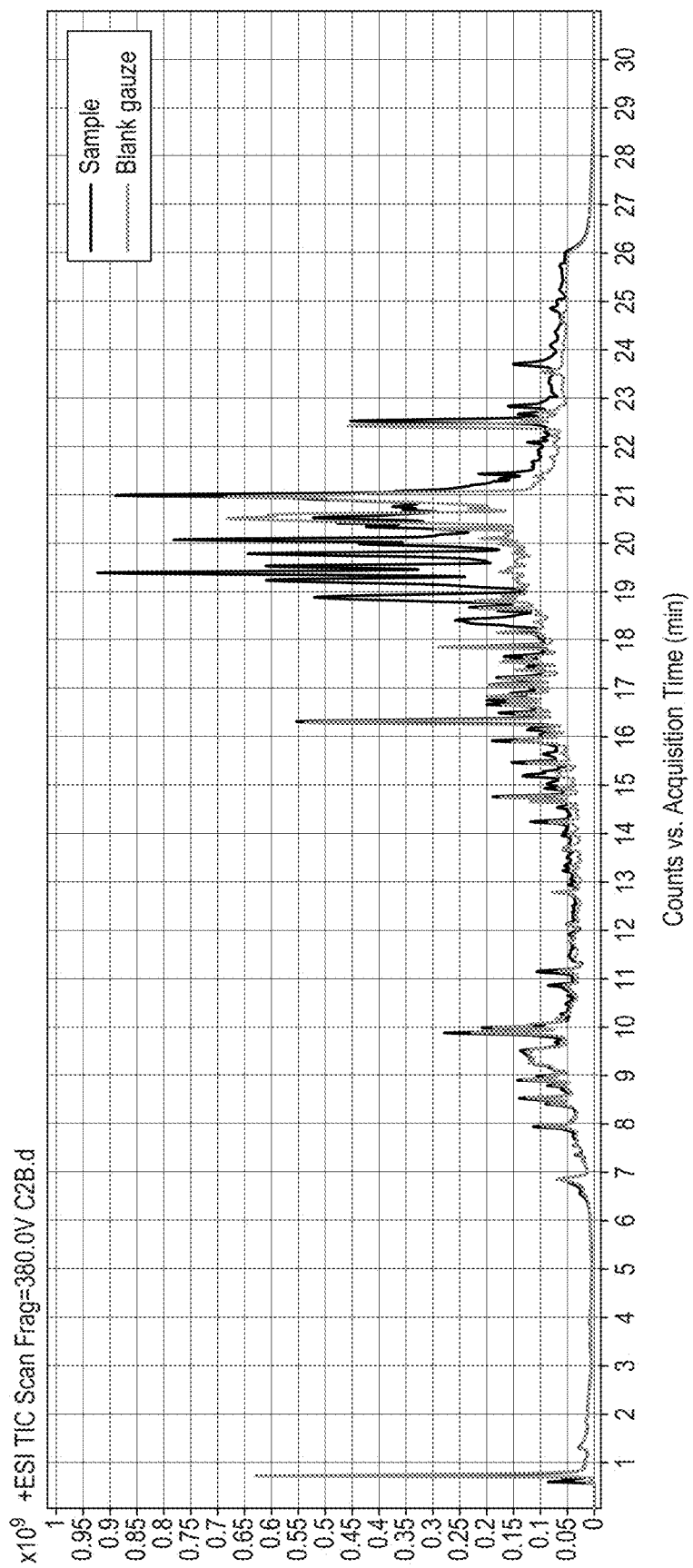
FIG. 6 shows a plot of blank gauze vs sample reconstituted in $H_2O$:MeOH (50:50)
Figure 7:
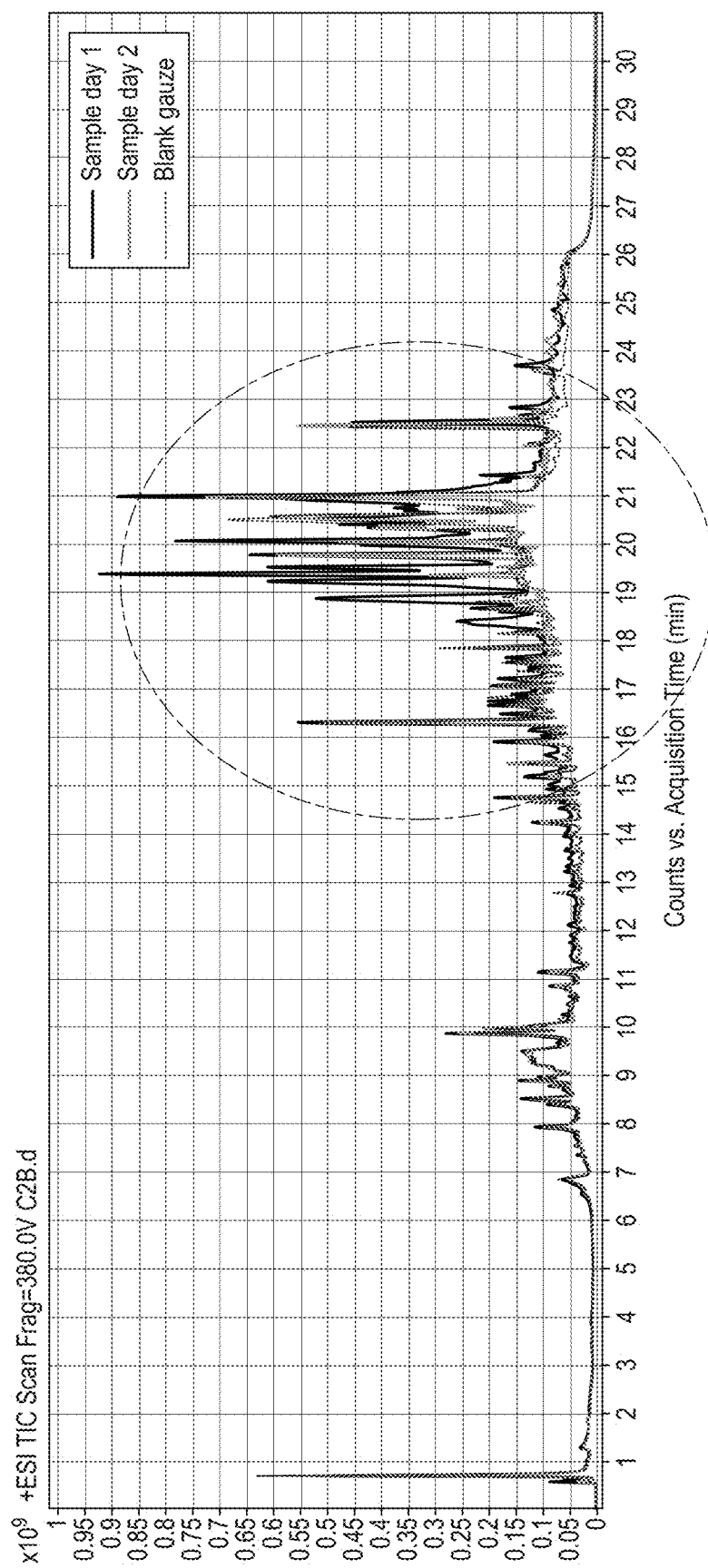
FIG. 7 shows a plot of blank gauze vs day 1 sample vs day 2 sample (same subject) reconstituted in $H_2O$:MeOH (50:50)
Figure 8:
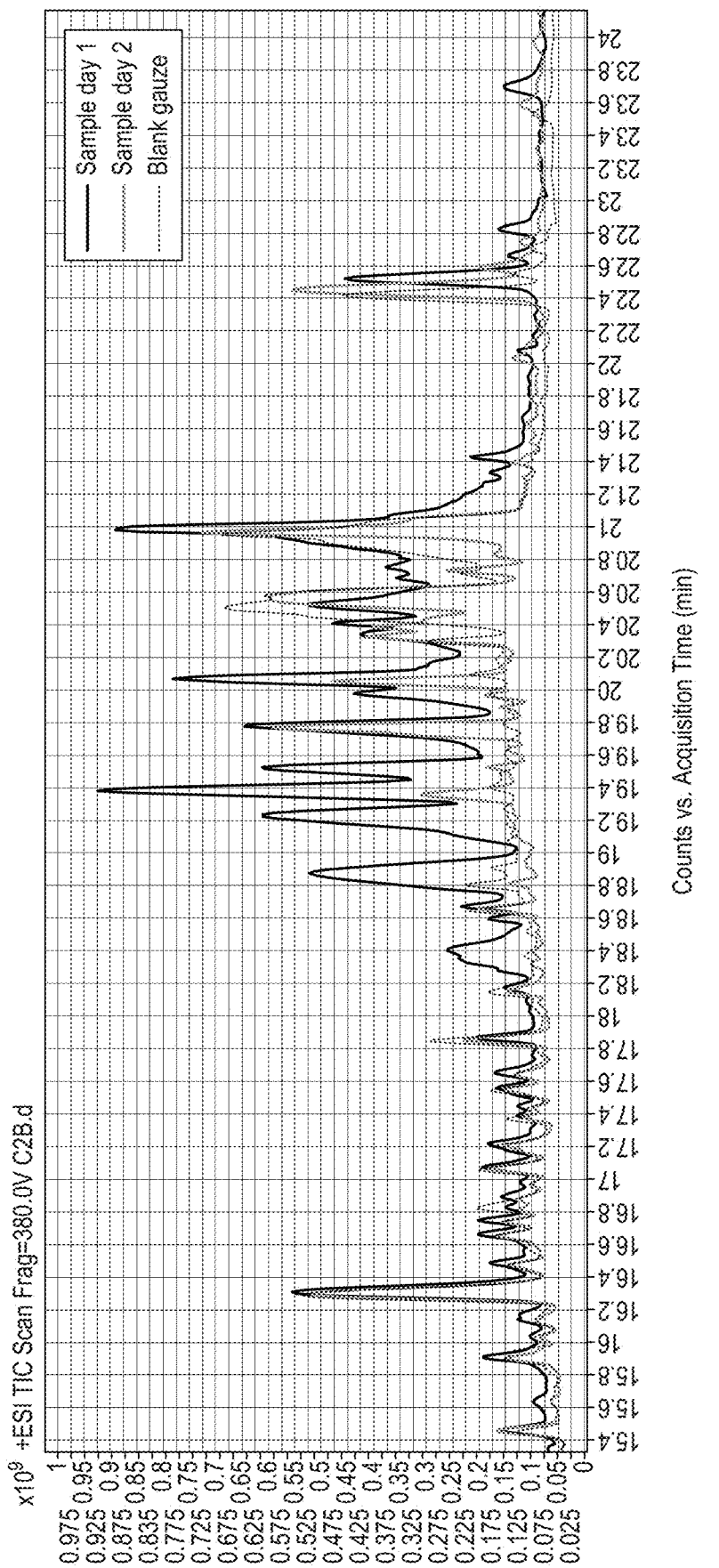
FIG. 8 shows a zoomed in region of the plot of FIG. 7 (15 min-24 min)
Figure 9:
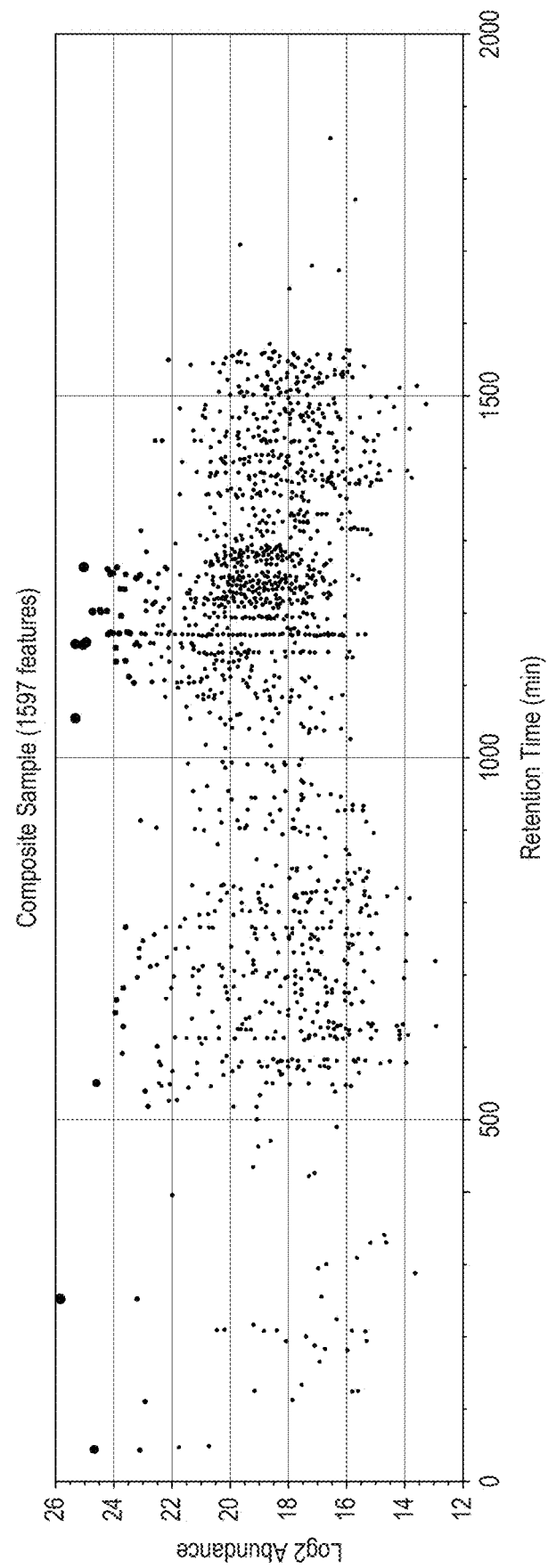
FIG. 9 shows a plot of XCMS based deconvolution.
Figure 10:
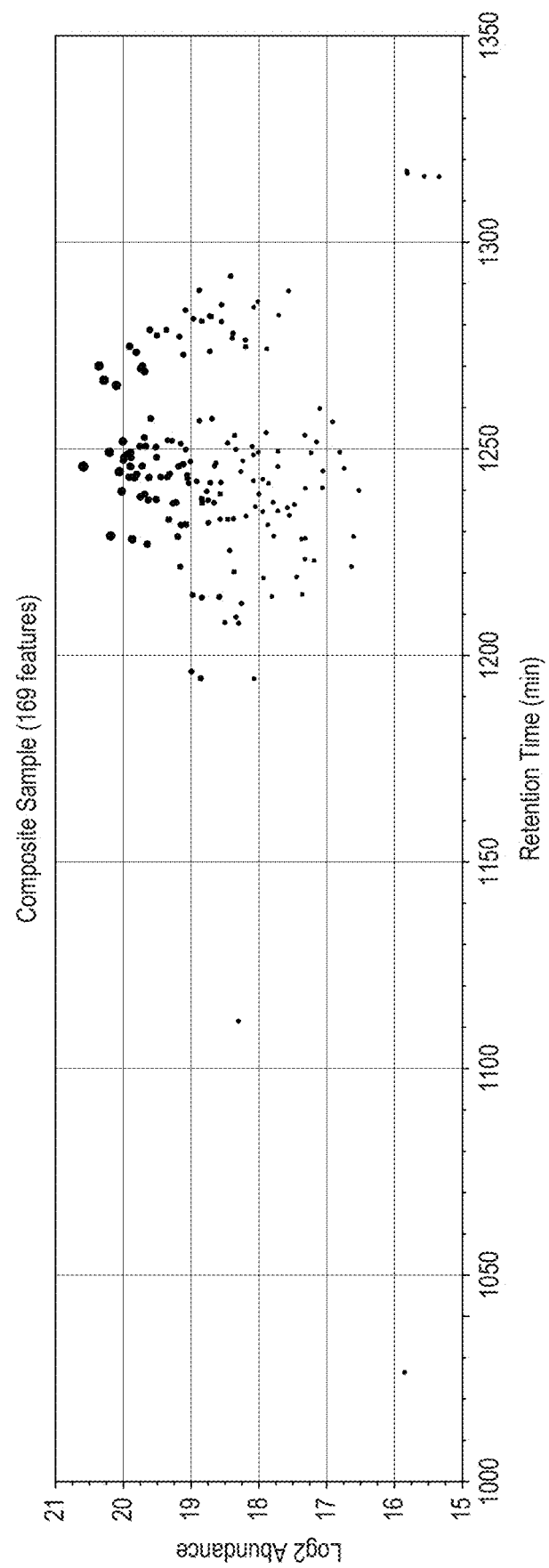
FIG. 10 shows a plot of features unique to samples only.
Figure 11:
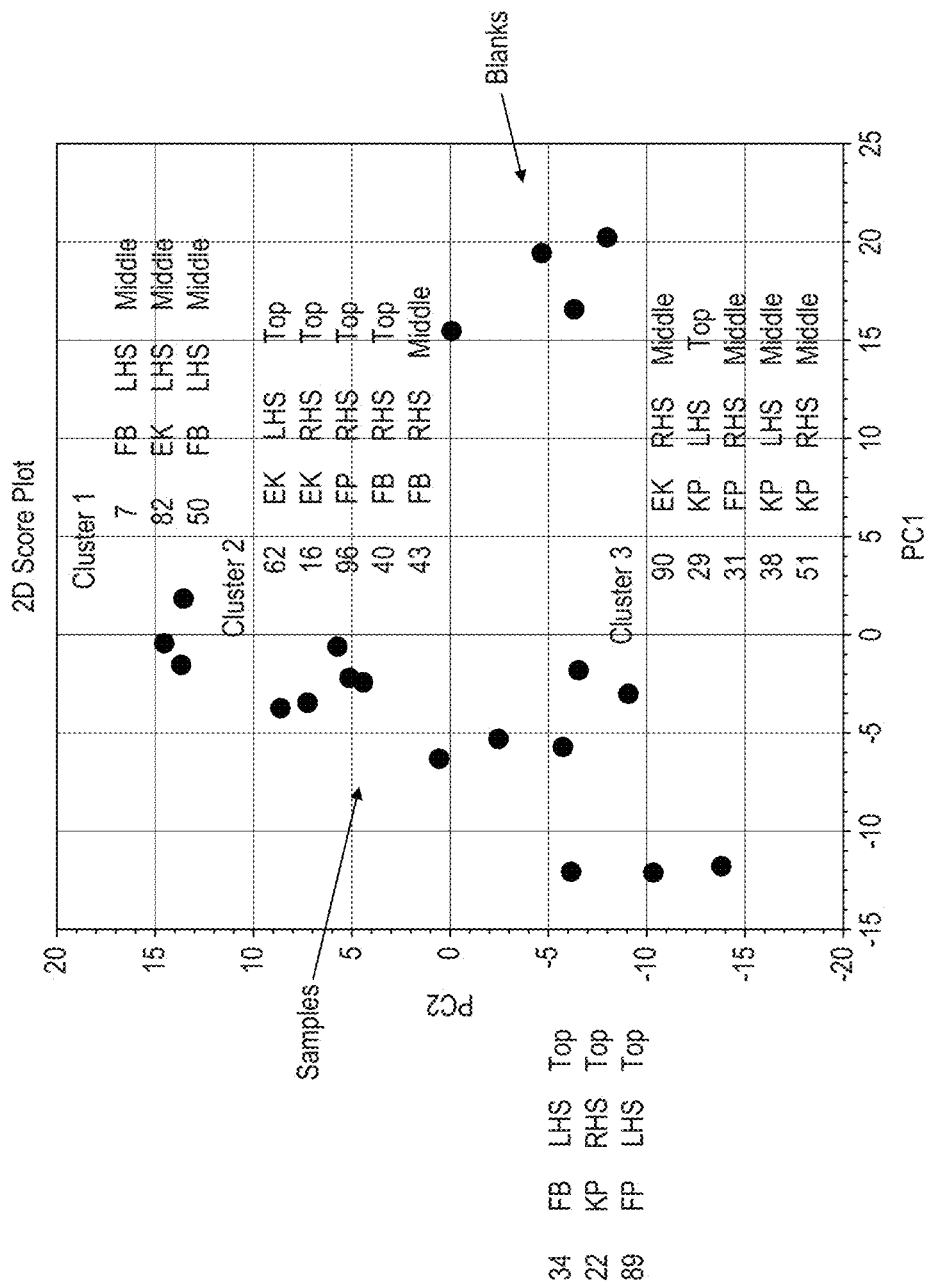
FIG. 11 shows a plot of methanol 9 mL data.
Figure 12:
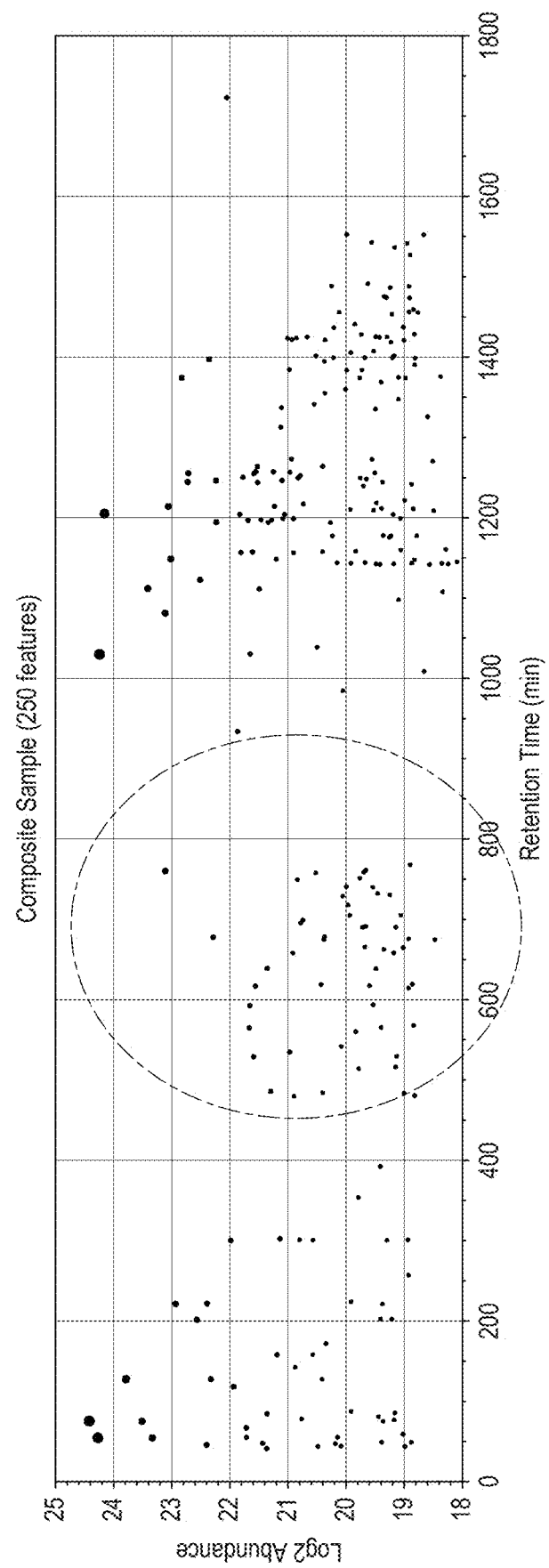
FIG. 12 shows a plot of potential PEG area.

The study design is also outlined in FIG. 4.

Sample Collection

The sampling involved each subject being swabbed on the upper back with a medical gauze. The gauze with sebum sample from participant's upper back was sealed in background-inert plastic bags and transported to the central facility, where they were stored at −80° C. until the date of analysis.

TD-GC-MS Analysis

Description of the Technique

A Dynamic Headspace (DHS) GC-MS method was developed for the analysis of gauzes used to swipe skin of PD affected individuals. DHS is a sample preparation capability for subsequent GC application using the GERSTEL Multi-Purpose Sampler (MPS). DHS extracts and concentrates VOCs from liquid or solid samples. The sample is incubated while the headspace is purged with a controlled flow of inert gas through an adsorbent tube. Once extraction and pre-concentration is completed, the adsorbent tube is automatically desorbed using the GERSTEL Thermal Desorption Unit (TDU). Analytes are then cryo-focused on the GERSTEL Cool Injection System (CIS) PTV injector before being transferred to the GC for analysis.

In order to correlate the PD molecular signature to the PD smell, the same setup was used in combination with the GERSTEL Olfactory Detection Port (ODP). The ODP allows detection of odorous compounds as they elute from the GC by smell. In fact, the gas flow is split as it leaves the column between the detector of choice (in our case MS) and the ODP to allow simultaneous detection on the two analytical tools. The additional smell profile information can then be acquired. Voice recognition software and intensity registration allow direct annotation of the chromatogram.

Method Details

Gauzes were transferred into 20 mL headspace vials and then analysed by DHS-TDU-GC-MS. For the DHS pre-concentration step, samples were incubated for 5 min at 60° C. before proceeding with the trapping step. Trapping was performed purging 500 ml of the sample headspace at 50 mL·min$^{-1}$ through a Tenax® TA adsorbent tube kept at 40° C. (GERSTEL, Germany). Nitrogen was used as purge gas. To release the analytes, the adsorbent trap was desorbed in the TDU in splitless mode. The TDU was kept at 30° C. for 1 min then ramped at 720° C.·min$^{-1}$ to 250° C. held for 5 min. Desorbed analytes were cryofocused in the CIS injector. The CIS was operated in solvent vent mode, using a vent flow of 80 mL·min$^{-1}$ and applying a split ratio of 10. The initial temperature was kept at 10° C. for 2 min, then ramped at 12° C.·s$^{-1}$ to 250° C. held for 10 min. The GC analysis was performed on an Agilent GC 7890B coupled to an Agilent MSD 5977B equipped with high efficiency source (HES) operating in EI mode. Separation was done an Agilent HP-5 MS Ultra inert 30 m×0.25 mm×0.25 µm column. The column flow was kept at 1 mL·min$^{-1}$. The oven ramp was programmed as following: 40° C. held for 5 min, 10° C.·min$^{-1}$ to 170° C., 8° C.·min$^{-1}$ to 250° C., 10° C.·min$^{-1}$ to 260° C. held for 2 min for a total run time of 31 min. The transfer line to the MS was kept at 300° C. The HES source was kept at 230° C. and the Quadrupole at 150° C. The MSD was operated in scan mode for mass range between 30 and 800 m/z. For the olfactometry approach, the chromatographic flow was split between the mass spectrometer and the GERSTEL Olfactory Detection Port (ODP3) using Agilent Technologies Capillary Flow Technology (three-way splitter plate equipped with make-up gas). The ODP3 transfer line was kept at 100° C. and humidity of the nose cone was maintained constant.

Data Pre-Processing and Deconvolution

TD-GC-MS data were converted to open source mzXML format using ProteoWizard. Each cohort data was deconvolved separately using in-house XCMS script written in R. The deconvolved analytes were assigned putative identifications by matching fragment spectra with compound spectra present in Golm database, NIST library and Fiehn GCMS library. The resulting matrices for each cohort consisted of variables and their respective area under the peak for each sample. All data were normalised for age and total ion count to account for confounding variables (see Table 2). The data was log-scaled and Pareto scaled prior to Wilcoxon-Mann-Whitney analysis, PLS-DA and the production of ROC curves as described.

Results

In the current study, VOCs from the sample headspace were measured in two cohorts: —a 'discovery' cohort and a 'validation' cohort, as suggested for biomarker discovery using metabolomics [21], each consisting of 30 subjects (for demographics see Table 2). A third cohort consisting of three drug naïve PD participants was used for mass spectrometry analysis in conjunction with a human Super Smeller via an odor port. This proof of principal study provides the first description of the skin volatilome in Parkinson's disease.

Figures 1A, 1B:
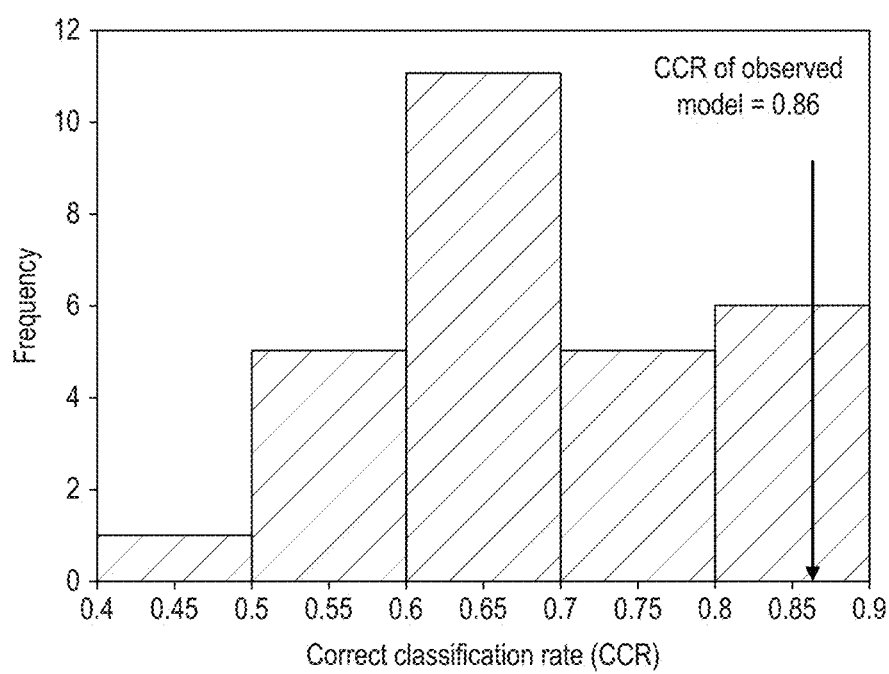

The mass spectrometry data were collected, deconvolved and pre-processed as described. Partial least squares discriminant analysis (PLS-DA) models were built using the discovery cohort data (FIG. 1). This modeling was validated with 5-fold cross validation (averaged correct classification rate (CCR) of 86%) as well as 26 permutation tests (averaged permutated CCR of 68%, averaged CCR of 83%, p-value<0.1). The variables contributing to classification (n=17) were selected using variable importance in projections (VIP) scores where VIP>1. The measured volatilome in the validation cohort data (from a different population than the discovery phase) was targeted for the presence or absence of these discovered biomarkers. Nine out of 17 metabolites were also found in the validation cohort data (Table 3 below).

TABLE 3

List of candidate volatiles putatively identified (MSI level 2) ands matched across two different cohorts. Nine of out 17 metabolites listed were selected for further analysis since they had acceptable retention time drift between the two sets of experiments.

| Putative identification | Mass | Retention time (discovery) | Retention time (validation) | Retention time difference | Comments |
| --- | --- | --- | --- | --- | --- |
| dodecane | 170.34 | 13.20 | 13.27 | −0.07 | Included |
| eicosane | 282.56 | 20.65 | 20.62 | 0.03 | Included |
| octacosane | 394.77 | 17.49 | 17.46 | 0.03 | Included |
| hippuric acid | 179.17 | 20.61 | 20.52 | 0.09 | Included |
| octadecanal or dodecane | 170.34 | 20.87 | 20.75 | 0.12 | Included |
| artemisinic acid | 234.34 | 12.97 | 12.83 | 0.14 | Included |
| perillic aldehyde or diglycerol | 150.22 | 11.82 | 11.66 | 0.15 | Included |
| hexyl acetate or dodecane | 170.34 | 11.70 | 11.53 | 0.16 | Included |
| 3-hydroxytetradecanoic acid or octanal | 244.38 | 11.58 | 11.32 | 0.26 | Included |
| gallic acid ethyl ester | 198.17 | 11.40 | 10.99 | 0.41 | Excluded |
| cyclohexasiloxane, dodecamethyl | 357.57 | 16.47 | 16.06 | 0.41 | Excluded |
| proline | 115.13 | 14.27 | 13.77 | 0.50 | Excluded |
| glutamine[-$H_2O$] | 128.09 | 21.73 | 21.09 | 0.64 | Excluded |
| cyclohexylcyclohexane | 357.57 | 15.36 | 14.71 | 0.65 | Excluded |
| tetracosane | 338.65 | 18.17 | Not found | n/a | Not found |
| 3,4-dihydroxy mandelic acid | 184.15 | 20.87 | Not found | n/a | Not found |
| neoabietic acid | 302.46 | 21.66 | Not found | n/a | Not found |

Figure 2B:
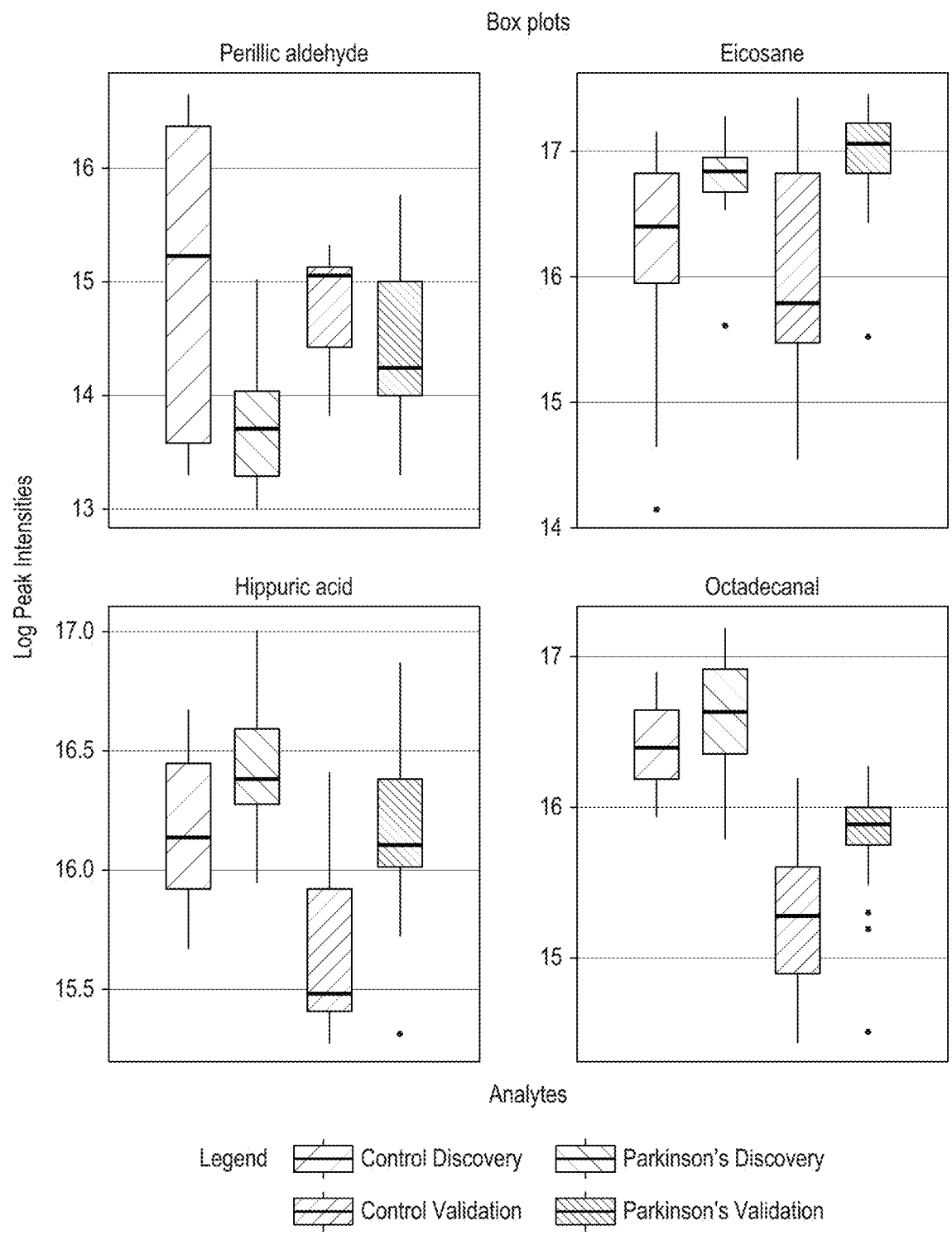
Figure 2C:
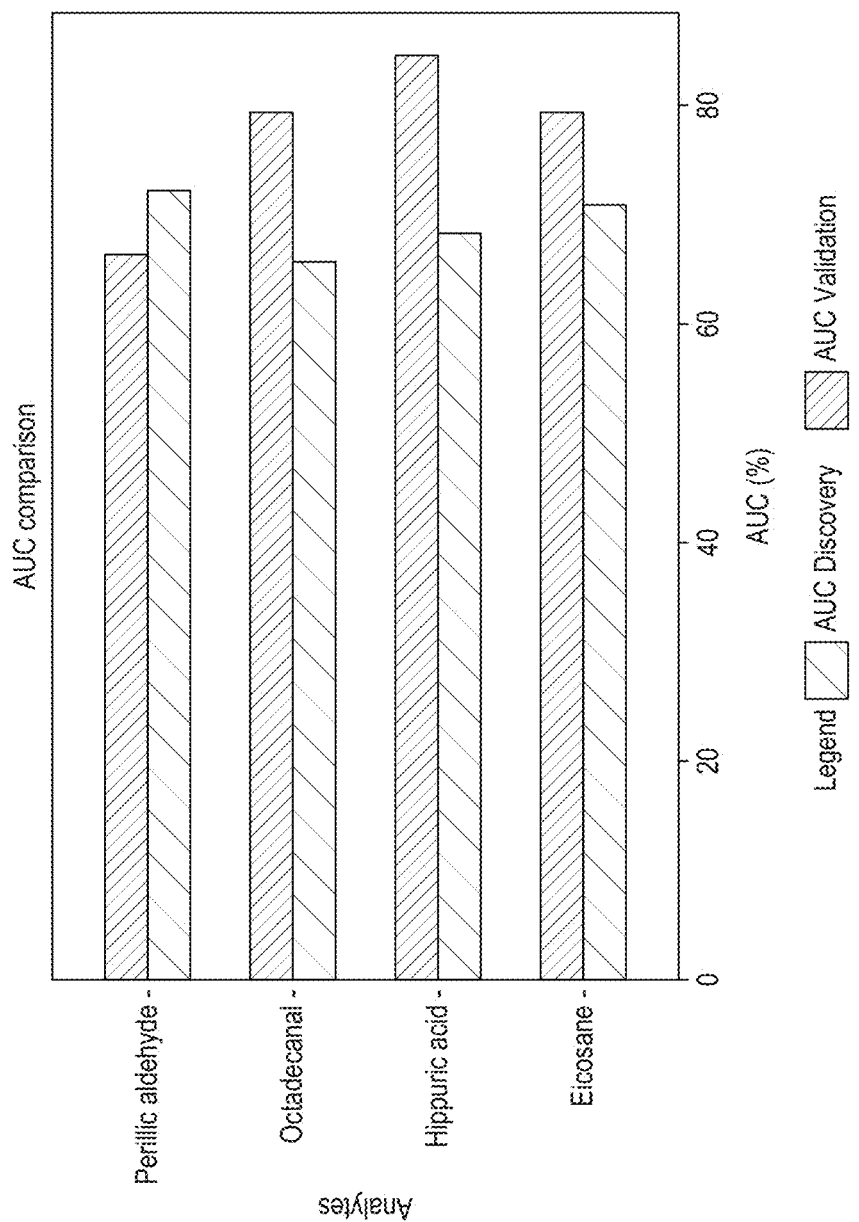

These nine common biomarkers were selected for further analysis and statistical testing. To evaluate the performance of these common biomarkers from our discovery and validation cohort data, receiver operating characteristic (ROC) analysis was conducted with data from both the discovery cohort and the validation cohort. ROC curves and Wilcoxon-Mann-Whitney test as well as fold-change calculations on individual metabolites shows four out of these nine common metabolites had similar expression in PD between discovery and validation cohort and their performance was also similar as measured by AUC between discovery and validation cohort (see Table 4 below and FIG. 2).

TABLE 4

| Putative identification | Parent Mass | ΔRT (min) | FDR corrected p-value (Mann-Whitney test) | | | Expression (PD/Control) | |
| --- | --- | --- | --- | --- | --- | --- | --- |
| | | | Discovery | Validation | Combined | Discovery | Validation |
| Perillic aldehyde | 150.22 | 0.15 | 0.0279 | 0.0403 | <0.0001 | Down | Down |
| Hippuric acid | 179.17 | 0.09 | 0.1908 | 0.0403 | 0.1833 | Up | Up |
| Eicosane | 282.56 | 0.03 | 0.0279 | 0.0403 | 0.0013 | Up | Up |
| Octadecanal | 170.34 | 0.12 | 0.2605 | 0.0604 | 0.3040 | Up | Up |

Panel of four volatile metabolites that were found to be differential between Parkinson's and control samples, with similar trends observed in expression and AUC curves measured by ROC analyses.
Perillic aldehyde and Eicosane were significantly down-regulated and up-regulated in PD, respectively (FDR corrected p <0.05).

MSI (Metabolomics Standards Initiative) guidelines for data analysis were adhered to and for assignment of identity to features of interest [22]. All of our identified features were at MSI level two [22]. Perillic aldehyde and eicosane were significantly different between PD and control in both the cohorts (p-value<0.05): perillic aldehyde was observed to be lower in PD samples whereas eicosane was observed at significantly higher levels. Although hippuric acid and octadecanal were not significantly different (p>0.05), the AUC (FIG. 2*a*) and box plots (FIG. 2*b*) between the two cohorts were comparable, showing similar trends.

Figure 3:
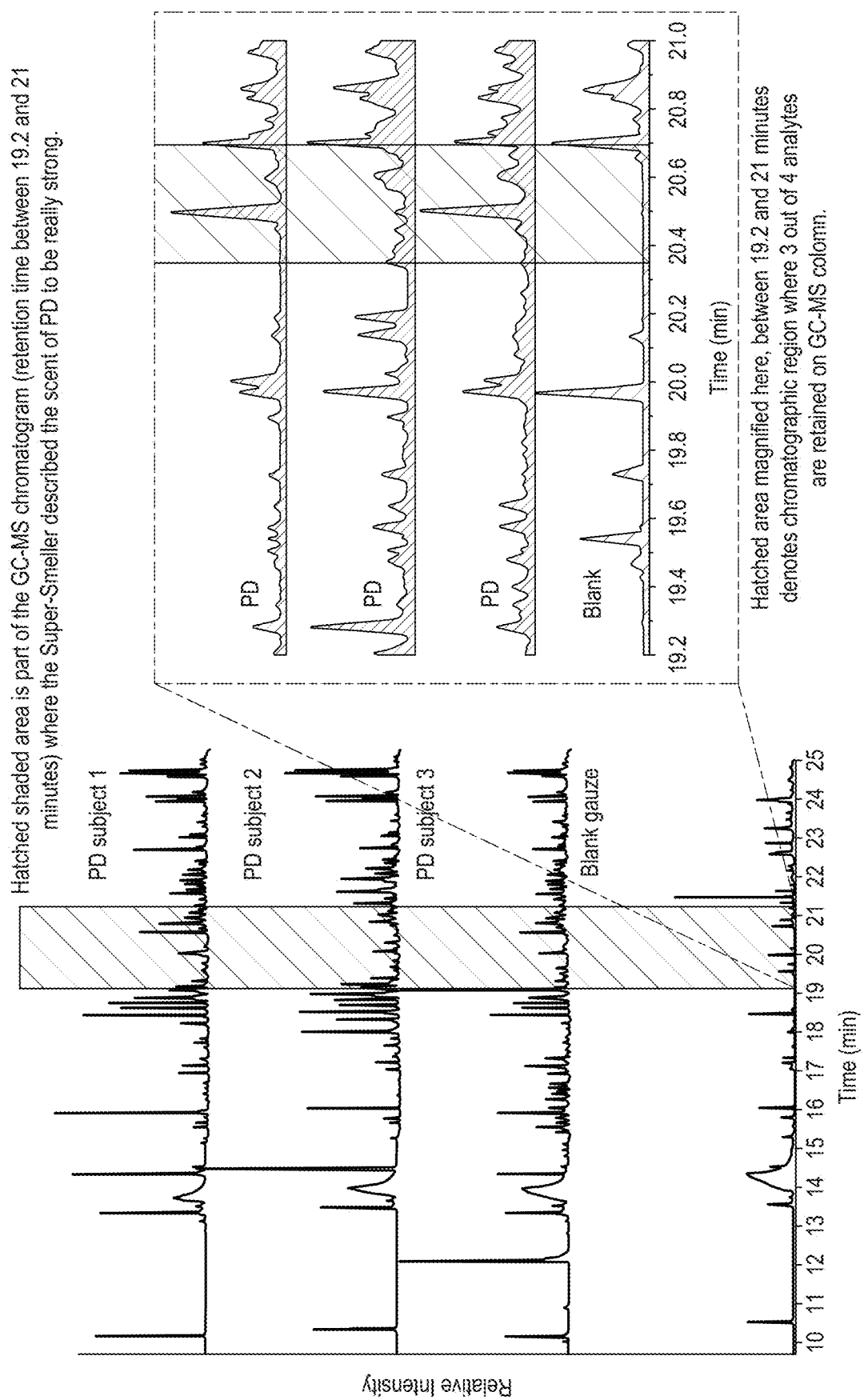

The samples from both cohorts were combined, thus increasing sample size and providing better statistical power while evaluating the performance of this panel of biomarkers. ROC curves were generated by Monte-Carlo cross validations (MCCV) using balanced sub-sampling. In each of the MCCV, two thirds of the samples were used to evaluate the feature importance. The top two, three, five, seven and nine important features were then used to build classification models, which were validated using the remaining one third of the samples. The process was repeated 500 times to calculate the average performance and confidence interval of each model. Classification and feature ranking was performed using a PLS-DA algorithm using two latent variables (FIG. 4). The results from the combined data indicate increased confidence in the data (p-values in Table 1 and confidence intervals in FIG. 1). When Olfactograms obtained from the odour port were overlaid on the total ion chromatograms (FIG. 3), many regions of interest (ROI) were identified. Due to individual variations between the subjects, both in their exosome and endosomes, the perceived smell is expected to have variations between participants. However, several ROIs were consistently similar between the samples further indicating a similarity between PD individuals. The ROI between 19 and 21 min of the chromatographic run is of particular interest since the smell associated with the mixture of analytes between that retention window was described as "very strong" and "musky"—the scent of PD. This is the same region where three out of four common volatiles between the two cohorts have been detected viz. hippuric acid, eicosane and octadecanal. It should also be noted here that all three of these volatiles were up regulated in PD subjects. This may indicate that the presence of one or more of these compounds could be associated with the scent of PD.

From these results obtained from three independent sets of data, from different people with one underlying factor (i.e. PD) separating them, it was clear that several volatile features were found to be significantly different between control and PD participants. There were no significant differences observed between PD participants on medication and drug naïve PD participants, indicating that the majority of the analysed volatilome may not contain drug metabolites or sebum may be devoid of high concentrations of drug metabolites that can be associated with PD medication. Perillic aldehyde and octadecanal are ordinarily observed as plant metabolites or food additives. It can be hypothesised that with irregular sebum secretion these lipid-like hydrophobic metabolites may be altered on the skin of PD subjects. Such effects could be attributed to a direct change in metabolism resulting in dysregulated excretion of dietary metabolites such as eicosane in sebum or could be attributed to a metabolic change in PD skin, that may affect the skin microflora causing changes in the production of metabolites such as hippuric acid [23]. These observed effects may also be an indirect or secondary observation to the physiological manifestation of PD. This study highlights the potential of comprehensive analysis of sebum from PD patients and raises the possibility that individuals can be screened non-invasively based on their scent.

Example 2—Gauze—Optimization of Extraction Protocol for Metabolomics

Experiments were conducted to optimize and assess extraction protocol for gauze impregnated samples.
Extraction Procedure
For the extraction, 9 mL Toluene was added, falcon tube shaken for 1 hr, gauze hooked over metal wire and centrifuged for 10 mins (1500 rpm), dry gauze removed. For each extraction the solvent was split into 2× eppendorfs (1xLC, 1xGC) and dried down using a speedvac.
Comparison
The following comparisons were assessed:
Blank gauze vs sample reconstituted in $H_2O$:ACN (50:50)
Blank gauze vs sample reconstituted in $H_2O$:MeOH (50:50)
Blank gauze vs day 1 sample vs day 2 sample (same subject)
Blanks vs Sample (irrespective of resuspension method)
In total, 4 samples and 2 blanks were tested. The details of the extraction comparison experiments are shown in Table 5 below.

TABLE 5

| ID | Location | Day Taken | Samples Run | Reconstitution (200 uL) |
|---|---|---|---|---|
| 501 | Top RHS | 1 | 501 | $H_2O$:MeOH (50:50) |
| 505 | Top RHS | 1 | 505 | $H_2O$:ACN (50:50) |
| 503 | Top RHS | 2 | 503 | $H_2O$:MeOH (50:50) |
| 504 | Top RHS | 2 | 504 | $H_2O$:MeOH (80:20) |
| C1B | — | — | C1B | $H_2O$:ACN (50:50) |
| C2B | — | — | C2B | $H_2O$:MeOH (50:50) |

Figure 13:
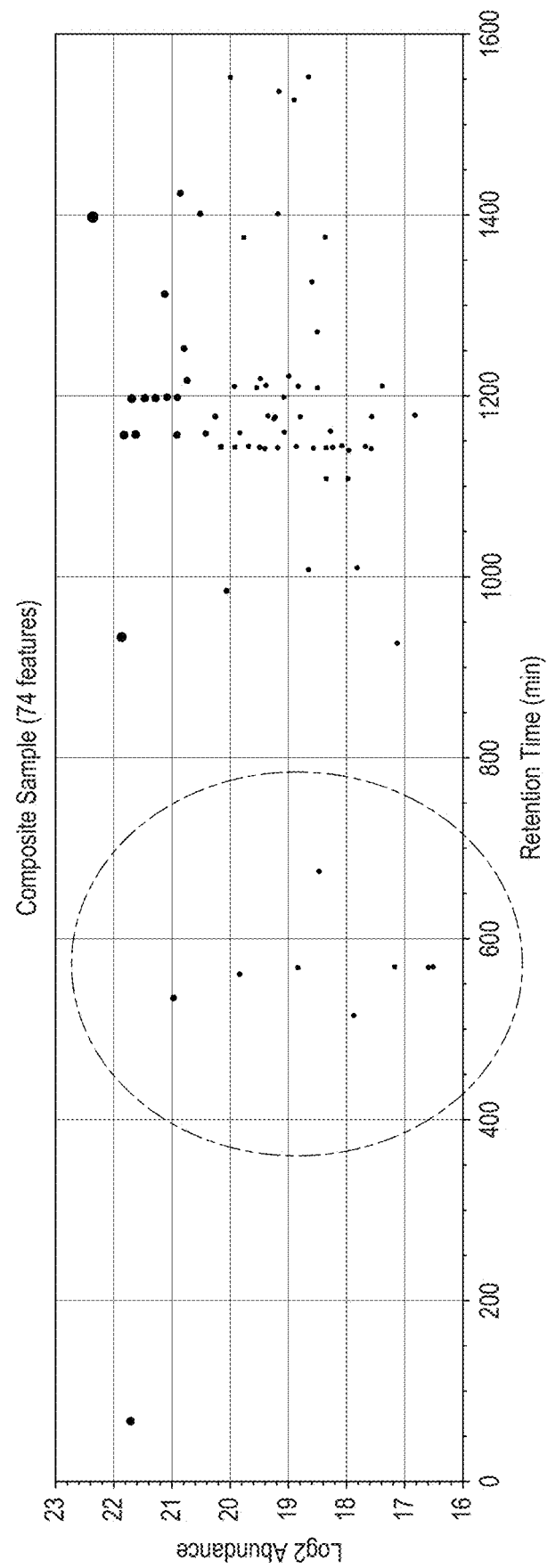
FIG. 13 shows a plot of the number of features higher in blank in the PEG area.

FIGS. 5 to 14 show the results of the comparison experiments. In particular, FIG. 13 shows that if the PEG background was interfering with signal, we would expect to see a lot more metabolite here because in this graph we are plotting any peak that is 2 folds higher i.e. considered as a very high noise. The signal seems to be higher in the same RT region, where high PEG was suspected. This indicates we can safely eliminate any gauze related background issues.

FIG. 14 shows Granted approximately 10 features are masked by PEG, we have about a hundred that aren't i.e. signal-to-noise ratio is much higher and any PEG-like contamination that may come off from gauze can be avoided by this extraction.

Example 3—Extraction Protocol Optimisation

Experiments were conducted in order to optimize the extraction protocol using different solvents.
Toluene Extraction
Toluene was established as not compatible with filters for the removal of gauze residue. Toluene cannot be removed in speedvac-especially in such high volumes. It was found to damage the seals on common speedvacs in labs.
Especially for scaling the procedure to high sample numbers: evaporation in a fume-hood would not be feasible and leaving eppendorfs (with no lid) over long periods in communal labs is not good practice. Whilst, using a heat block to speed up removal of the solvent was assessed, this did not speed up the evaporation to a reasonable speed at lower temperatures and high temperatures could be detrimental to sample integrity.
Due to these issues, the reconstitution composition was difficult to optimise, and was not consistent between samples.
FIG. 15A shows that solid residue formed during reconstitution in Toluene:Methanol (20:80). The addition of chloroform followed by centrifugation (x2 steps) allowed a clear supernatant to be obtained.
FIG. 15B shows that solid substance was formed on reconstitution in Toluene:Methanol (50:50).
Folch Extraction
It was assessed that this solvent combination was not compatible with filters to remove gauze residue. The chloroform layer for LC-MS did not reconstitute back into Water:Methanol (80:20) and formed a cloudy solution
Whilst adding chloroform during reconstitution was assessed, too much volume was needed to be viable, multiplying the number of centrifugation cycles lost too much sample
Methanol Extraction
In this extraction protocol, 9 mL, 15 mL and 20 mL solvent extraction volumes were tested. It was established that the lower solvent yielded the highest signal and that a minimum of 9 mL was needed due to the gauze size the volume of solvent it absorbs.
Ordinarily the samples extracted in organic solvents, can be reconstituted back into organic solvents. For example, samples extracted in methanol and then dried down to form a pellet should normally reconstitute back in methanol and also ethanol, acetonitrile or isopropanol. However, we have discovered that lipids and lipid-like molecules extracted by our protocol, tend to destabilise under methanol over long period of time. In metabolomics, or LC-MS analyses, the norm is to reconstitute the extracts in various combinations (%) of water and methanol. However, this destabilised our analytes and it ended up forming solid residues shown in above photos, after a short period of time. This was reproduced even when the samples were stored at ambient temperature and on a cold tray. A mixture of organic solvents was assessed and methanol and ethanol (50:50 v/v) stabilises the reconstituted sebum. This indicates that the molecules extracted from sebum are atypical and requires a combination of organic solvents as opposed to organic-aqueous mixture or single organic solvent to stay in solution.

Example 4—Preferred Extraction Protocols

It was therefore established that the following extraction protocol had the best performance:
Q-Tip Extraction
1. Snap wooden stem of QTip into a 2 mL eppendorf
2. Add 1 mL MeOH
3. Vortex for 10 seconds
4. Sonicate for 10 minutes
5. Remove QTip
6. Centrifuge for 5 mins
7. Pipette 800 µL into a new eppendorf (split in half if needing two fractions)
8. Dry in speedvac concentrator for ~6 hrs
9. Store in −80 deg freezer Gauze Extraction
1) Using tweezers place gauze in 50 mL falcon tube
2) Add 9 mL methanol, shake till gauze is at bottom of tube
3) Vortex for 10 seconds
4) Sonicate for 30 minutes
5) Pipette extracted methanol from gauze tube
6) Use a syringe and filter for the extracted solvent into a new tube-recovery ~7 mL
7) Split this into 3×2 mL fractions in eppendorfs
8) Dry for ~10/12 hrs using speedvac concentrator
8) Store in −80 deg Example 5—Paper Spray Ionization Mass Spectrometry of Human Sebum for Parkinson's Disease Diagnostics Study Participants For initial method development of paper spray ionization mass spectrometry (PSI-MS) using sebum, samples from healthy controls were used. After achieving a satisfactory reproducibility of the mass spectra collected from human sebum, the method was further tested using samples from participants with Parkinson's disease. The participants for this study were part of a recruitment process taking place at 28 different NHS clinics all over the UK. A subset from a larger recruitment drive was used for this work (65 PD and 52 control samples) collected from a local clinic (also involved in Parkinson's disease research).

Sample Collection

Sebum samples were non-invasively swabbed from the upper/lower back of participants with medical Q-tip swabs. Then the Q-tip swabs with the sebum sample were secured in their individual caps and transported in sealed envelopes to the central facility at the University of Manchester where they were stored at −80° C. until the date of analysis.

Method: Paper Spray Ionization Mass Spectrometry (PSI-MS)

For all PSI-MS experiments, commercially available Whatman filter papers (grade 1 and 42) were used as the paper substrates. Sebum samples were transferred from the Q-tip swabs to the paper substrates by a gentle rub. After sample transfer, the paper was cut into a triangle (5 mm at the base and 10 mm in height). Then the paper triangle was carefully clipped to a copper alligator clip using tweezers. Careful handling of the paper was important to avoid contamination. The copper clips were cleaned by sonication in acetone before use. For each sample, a new clip and tweezers were used to avoid cross-contamination across the samples. Then the clip was connected to a home-built paper spray holder which was adapted to an existing mass spectrometer for PSI-MS measurements followed by placing the holder in front of the MS inlet using an adjustable stage. The holder was adjusted in such a way that the paper tip is at a 5-7 mm distance from the MS inlet. After placing the paper triangle at a desirable position, a high voltage in the range of 2.5-3 kV was applied to it through the clip. When the paper, held at an elevated potential, was eluted with a polar solvent, a Taylor cone formation was observed at the tip of the paper which was immediately followed by observable m/z signals in the instrument software. All the mass spectra were recorded in the range of 50-2000 m/z. The main instrumental parameters for each PSI-MS experiment were set as capillary voltage 3 kV, source temperature 100° C., sampling cone 30 V and source offset 40 V. No desolvation or cone gas was used.

Use of Internal Standard

To check the reproducibility of paper spray across different samples, an internal standard was used. For these experiments, 3.5 µL of the internal standard solution was spotted on paper triangles and ambiently air dried. Dried paper triangles were used for PSI-MS measurements of sebum samples following an identical method described in the previous paragraph.

Data Processing

The data were recorded in Waters proprietary format. Total analysis time per sample was 120 scans in 2 minutes. These 120 scans were aggregated as a single, combined spectrum. The combined spectrum was recorded in a tabulated format for each sample such that each row had the m/z value measured and the absolute ion count. These data were generated for all the files in the experiment. The data were then saved in .csv format for each file individually.

Further data processing was done using the open-source statistical software R. In-house script was written to import .csv files into R as a data frame. Each m/z was binned using two steps-firstly, if the m/z was unique in a sample, it was preserved and if the m/z had already been detected in a previous sample, it was combined. The resulting data frame had all the possible m/z values detected across the entire dataset. In the next step, m/z values were rounded to the most accurate representation of instrumental measurement i.e. up to 4 decimal places in Dalton mass. Finally, consecutive m/z values were considered to be representative of the same ion if they were identical and their peak areas were summed. The resultant data were combined into a single matrix where each row showed an m/z value and the total ion count and each column represented a sample.

Data Analysis

Data reproducibility and quality were assessed using internal standard peak intensities for paper spray. Internal standard reference peaks were detected in all samples. The quality of data was determined by the coefficient of variance of internal standard peak ratios. A one-way t-test was used to determine significant differences between the means of each variable for control and PD samples. Every variable with $p<0.05$ was considered significant and was carried forward for putative identification. Putative identification was carried out by matching the m/z values with values in online databases-Human Metabolome Database (HMDB) and LipidMaps with a mass accuracy of 20 ppm.

Results and Discussion

FIG. 16 shows a schematic representation of the experimental workflow for analysing human sebum samples using the PSI-MS technique. Whatman grade 1 and 42 were used for PSI-MS analysis and both of the papers showed identical results (FIG. 17). Different solvents and solvent mixtures were tested for generating stable and reproducible spray. After a considerable number of tests, 4:1 $H_2O$/EtOH was chosen as the optimized solvent system for the best results in this particular study. The distance between the tip of the paper and the MS inlet was also optimized by trial and error.

After placing the paper tip at an optimum distance from the MS inlet, it was eluted with 4.5 μL of solvent. Mass spectra were recorded for two minutes at a scan rate of 2 sec/scan. A total of 60 scans was used for further data analysis. The inset of FIG. 16 shows a representative mass spectrum collected from human sebum. Mass spectra of human sebum show the presence of three envelopes at the higher mass region (m/z 1200-1800) consisting of singly charged peaks. PSI-MS has been used to detect small molecules present in biofluids like blood, urine, etc. This study, for the first time, shows that sebum can be used as a sampling biofluid for PSI-MS and that it enables the detection of skin surface molecules with a significantly higher molecular mass of <1200 m/z. Ion mobility-mass spectrometry (IM-MS) was also employed to further evaluate these high molecular weight metabolites and specifically to resolve conformational isomers and isobaric structural isomers as has been previously reported for lower molecular weight lipids (NATURE COMMUNICATIONS|(2019) 10:985|https://doi.org/10.1038/s41467-019-08897-5). FIG. 18 shows an example of the enhanced separation and diagnostic features (both in higher and lower mass regions) that can be found from the combination of ion mobility and mass spectrometry.

Figure 18C:
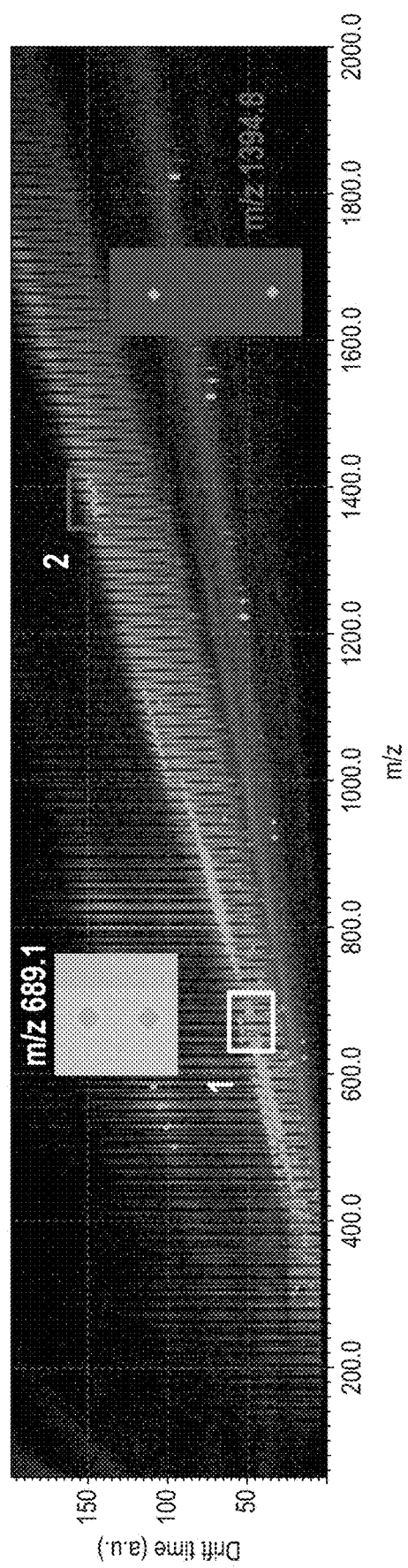

FIG. 18A shows a total ion chromatogram with respect to the arrival time distribution of different ions. The arrows indicate clear separation of the generated ions (identified as lipids) with respect to drift time. FIG. 18B shows the arrival time distribution of a single ion (m/z 689.1). The existence of two peaks on the drift time scale for a single m/z value indicates the possibility of the presence of an isomeric species. FIG. 18C shows a drift time vs m/z plot where the dots represent the m/z values. The dots (in the boxes labeled 1 and 2 respectively) in the insets show a zoomed view of m/z 689.1 (highlighted with box 1) and m/z 1394.8 (highlighted with box 2) which are separated in the drift time scale. This data shows that IM combined with PSI-MS could be used to separate gas-phase ions generated from human sebum samples.

After recording mass spectra from all of the participant samples under identical conditions, data were processed and statistical analysis was performed as outlined earlier. Table 6 shows the m/z values along with the probable molecular species of the statistically important molecules within our data. Interestingly, it was possible to identify a class of molecule known as cardiolipins (represented as CL in Table 6) which is predominant in the list of statistically important molecules.

TABLE 26

List of statistically important m/z values along with probable molecular species within our data set.

| m/z | Proposed molecule | Chemical formula | Possible ion |
|---|---|---|---|
| 1668 | CL(68:0) | $C_{77}H_{150}O_{17}P_2K$ | [M + K]+ |
| 1644 | CL(74:6) | $C_{83}H_{150}O_{17}P_2K$ | [M + K]+ |
| 1632 | CL(72:4) | $C_{81}H_{150}O_{17}P_2K$ | [M + K]+ |
| 1628 | CL(76:11) | $C_{85}H_{144}O_{17}P_2$ | |
| 1622 | CL(74:8) | $C_{83}H_{146}O_{17}P_2Na$ | [M + Na]+ |
| 1620 | CL(72:5) | $C_{81}H_{148}O_{17}P_2Na_2$ | [M + 2Na − H]+ |
| 1616 | CL(70:2) | $C_{79}H_{150}O_{17}P_2K$ | [M + K]+ |
| 1604 | CL(76:9) | $C_{85}H_{148}O_{17}P_2Na$ | [M + Na]+ |
| 1598 | CL(74:6) | $C_{83}H_{150}O_{17}P_2Na_2$ | [M + 2Na − H]+ |
| 1596 | CL(74:7) | $C_{83}H_{148}O_{17}P_2Na$ | [M + Na]+ |
| 1592 | CL(72:4) | $C_{81}H_{150}O_{17}P_2Na_2$ | [M + 2Na − H]+ |
| 1580 | CL(78:12) | $C_{87}H_{146}O_{17}P_2$ | |
| 1574 | CL(76:10) | $C_{85}H_{146}O_{17}P_2$ | |
| 1572 | CL(72:7) | $C_{81}H_{144}O_{17}P_2$ | |
| 1568 | CL(70:4) | $C_{79}H_{146}O_{17}P_2Na$ | [M + Na]+ |
| 1556 | CL(68:1) | $C_{77}H_{148}O_{17}P_2Na_2$ | [M + 2Na − H]+ |
| 1550 | CL(78:10) | $C_{87}H_{150}O_{17}P_2Na_2$ | [M + 2Na − H]+ |
| 1548 | CL(78:12) | $C_{87}H_{146}O_{17}P_2Na$ | [M + Na]+ |
| 1548 | CL(76:9) | $C_{85}H_{148}O_{17}P_2Na_2$ | [M + 2Na − H]+ |
| 1532 | CL(72:6) | $C_{81}H_{146}O_{17}P_2$ | [M + H − H2O]+ |
| 1526 | CL(74:9) | $C_{83}H_{144}O_{17}P_2$ | [M + H]+ |
| 1526 | CL(72:6) | $C_{81}H_{146}O_{17}P_2Na$ | [M + Na]+ |
| 1520 | CL(70:3) | $C_{79}H_{148}O_{17}P_2Na_2$ | [M + 2Na − H]+ |
| 1511 | CL(76:8) | $C_{85}H_{150}O_{17}P_2Na_2$ | [M + 2Na − H]+ |
| 1508 | CL(72:5) | $C_{81}H_{148}O_{17}P_2Na$ | [M + Na]+ |
| 1502 | CL(70:2) | $C_{79}H_{150}O_{17}P_2Na_2$ | [M + 2Na − H]+ |
| 1502 | CL(74:8) | $C_{83}H_{146}O_{17}P_2$ | [M + H − H2O]+ |
| 1500 | CL(70:3) | $C_{79}H_{148}O_{17}P_2Na$ | [M + Na]+ |
| 1500 | CL(68:0) | $C_{77}H_{150}O_{17}P_2Na_2$ | [M + 2Na − H]+ |
| 1500 | CL(68:3) | $C_{77}H_{144}O_{17}P_2$ | [M + H]+ |
| 1496 | CL(66:0) | $C_{75}H_{146}O_{17}P_2Na$ | [M + Na]+ |
| 1488 | CL(78:10) | $C_{87}H_{150}O_{17}P_2K$ | [M + K]+ |
| 1484 | CL(68:1) | $C_{77}H_{148}O_{17}P_2Na$ | [M + Na]+ |
| 1478 | CL(70:5) | $C_{79}H_{144}O_{17}P_2$ | [M + H]+ |
| 1478 | CL(68:2) | $C_{77}H_{146}O_{17}P_2Na$ | [M + Na]+ |
| 1476 | CL(68:2) | $C_{77}H_{146}O_{17}P_2$ | [M + H − H2O]+ |
| 1476 | CL(66:1) | $C_{75}H_{144}O_{17}P_2$ | [M + H]+ |
| 1476 | CL(70:4) | $C_{79}H_{146}O_{17}P_2$ | [M + H − H2O]+ |
| 1472 | CL(80:12) | $C_{89}H_{150}O_{17}P_2Na_2$ | [M + 2Na − H]+ |
| 1466 | CL(66:0) | $C_{75}H_{146}O_{17}P_2$ | [M + H − H2O]+ |
| 1464 | CL(80:12) | $C_{89}H_{150}O_{17}P_2K$ | [M + K]+ |
| 1460 | CL(20:4) | | |
| 1454 | Ganglioside GM1 (d18:0/24:0) | | |
| 1454 | Dihydro-4-mercapto-3(2H)-furanone | | |
| 1452 | 2,3-Dihydrothiophene | | |
| 1452 | Methyl 2-furoate | | |
| 1452 | Ganglioside GM1 (d18:0/25:0) | | |

TABLE 26-continued

List of statistically important m/z values along with probable molecular species within our data set.

| m/z | Proposed molecule | Chemical formula | Possible ion |
|---|---|---|---|
| 1448 | 6-({5,7-dihydroxy-2-[4-hydroxy-3-(sulfooxy)phenyl]-4-oxo-4H-chromen-3-yl}oxy)-3,4,5-trihydroxyoxane-2-carboxylic acid | | |
| 1442 | Malic acid | | |
| 1440 | CL(84:19) | | |
| 1436 | 3-(3,4-dihydroxyphenyl)-2-(sulfooxy)propanoic acid | | |
| 1430 | CL(88:23) | | |
| 1428 | CL(68:0) | | |
| 1428 | | | |
| 1418 | CL(18:0/22:5(7Z, 10Z, 13Z, 16Z, 19Z)/20:4(5Z, 8Z, 11Z, 14Z)/22:5(4Z, 7Z, 10Z, 13Z, 16Z)) | | |
| 1416 | Trifluoroacetic acid | | |
| 1412 | CL(22:6(4Z, 7Z, 10Z, 13Z, 16Z, 19Z)/22:5(4Z, 7Z, 10Z, 13Z, 16Z)/22:6(4Z, 7Z, 10Z, 13Z, 16Z, 19Z)/22:5(4Z,7Z, 10Z, 13Z, 16Z)) | | |
| 1404 | CL(22:6(4Z, 7Z, 10Z, 13Z, 16Z, 19Z)/20:4(5Z, 8Z, 11Z, 14Z)/22:6(4Z, 7Z, 10Z, 13Z, 16Z, 19Z)/22:5(7Z, 10Z, 13Z, 16Z, 19Z)) | | |
| 1404 | Anagrelide (15 ppm) | | |
| 1388 | Uric acid | | |
| 1388 | CL(16:0/18:1(11Z)/16:0/18:1(11Z)) | | |
| 1380 | Bissulfine | | |
| 1368 | 4-Nitrophenyl phosphate | | |
| 1364 | Fluorouracil (21 ppm) | | |
| 302 | Phenylpropiolic acid | | |
| 301 | CL(16:0/22:6(4Z, 7Z, 10Z, 13Z, 16Z, 19Z)/22:6(4Z, 7Z, 10Z, 13Z, 16Z, 19Z)/22:5(4Z, 7Z, 10Z,13Z, 16Z)) | | |
| 285 | CL(22:5(4Z, 7Z, 10Z, 13Z, 16Z)/20:4(5Z, 8Z, 11Z, 14Z)/22:5(4Z, 7Z, 10Z, 13Z, 16Z)/20:4(5Z, 8Z, 11Z, 14Z)) | | |
| 284 | Malathion monocarboxylic acid | | |
| 257 | CL(i-13:0/i-21:0/i-17:0/i-16:0) | | |
| 256 | CL(i-13:0/i-20:0/i-18:0/18:2(9Z,11Z)) | | |
| 243 | N-Acetylglucosaminyl-diphosphodolichol | | |
| 220 | CL(i-13:0/i-21:0/i-17:0/i-16:0) | | |
| 215 | Sinalexin | | |
| 213 | CL(i-13:0/i-20:0/18:2(9Z, 11Z)/18:2(9Z, 11Z)) | | |
| 201 | CL(18:2(9Z, 12Z)/22:5(7Z, 10Z, 13Z, 16Z, 19Z)/22:5(7Z, 10Z, 13Z, 16Z, 19Z)/20:4(5Z, 8Z, 11Z, 14Z)) | | |
| 200 | CL(22:6(4Z, 7Z, 10Z, 13Z, 16Z, 19Z)/18:1(9Z)/22:6(4Z, 7Z, 10Z, 13Z, 16Z, 19Z)/18:1(9Z)) | | |
| 199 | N-Methylformamide | | |
| 185 | Dimethylthiophosphate | | |
| 173 | CL(a-13:0/18:2(9Z, 11Z)/i-22:0/18:2(9Z, 11Z)) | | |
| 171 | CL(a-13:0/i-22:0/18:2(9Z, 11Z)/18:2(9Z, 11Z)) | | |
| 157 | CL(i-13:0/i-20:0/i-18:0/18:2(9Z, 11Z)) | | |
| 141 | Mechlorethamine (10 ppm) | | |
| 131 | Dihydro-4-mercapto-5-methyl-3(2H)-thiophenone | | |
| 115 | 4-Ketocyclophosphamide | | |
| 113 | 3-Oxoglutaric acid | | |
| 98 | 1-benzofuran-4-ol | | |
| 96 | 4-Mercapto-5-methyl-3(2H)-thiophenone | | |
| 90 | S-Propyl thiosulfate | | |
| 88 | Risedronate (29 ppm) | | |
| 75 | Acrylic acid | | |
| 74 | Ethyl formate | | |
| 72 | Thelephoric acid | | |
| 71 | Thiophene (10 ppm) | | |
| 67 | trans-3-Chloro-2-propene-1-ol | | |
| 66 | 2-Furancarboxaldehyde | | |
| 59 | (4-ethenyl-2,6-dihydroxy phenyl)oxidanesulfonic acid | | |

A comparative study was performed between the PD and control samples considering these molecules. It was observed that these molecules are down-regulated in PD sebum. FIG. 19 shows the comparison of m/z 1668 and 1520 (putatively identified as cardiolipins) and m/z 1452 and 1454 (putatively identified as ganglioside) between PD and control samples.

Upon a closer look at the IM-MS data, a number of species could be identified that were up-regulated in the PD samples. Table 7 shows the m/z values and respective drift times for these species.

| | Drift time (ms) | | | |
|---|---|---|---|---|
| m/z | PD | | Control | |
| 815.6791 | 10.11 | 6.51 | 10.11 | absent |
| 829.6871 | 10.32 | 6.58 | 10.32 | absent |
| 843.6967 | 10.53 | 6.86 | 10.53 | absent |
| 857.7026 | 10.66 | 6.93 | 10.66 | absent |
| 867.7198 | 10.87 | 6.86 | 10.87 | absent |

Table 7. List of statistically important m/z values that are also significantly different (in PD samples vs controls) with respect to drift time.

FIG. 20 shows m/z vs drift time plots (data was averaged over 34 PD and 30 control samples) for the above ions. The arrows indicate the ions with the same m/z values but different drift times in PD samples (absent in controls). This data shows the potential of PSI-MS combined with ion mobility for Parkinson's disease diagnostics.

The forgoing embodiments are not intended to limit the scope of the protection afforded by the claims, but rather to describe examples of how the invention may be put into practice.

REFERENCES

1. DeMaagd, G. and A. Philip, *Parkinson's Disease and Its Management: Part 1: Disease Entity, Risk Factors, Pathophysiology, Clinical Presentation, and Diagnosis.* Pharmacy and Therapeutics, 2015. 40 (8): p. 504-532.
2. Cheng, H.-C., C. M. Ulane, and R. E. Burke, *Clinical Progression in Parkinson's Disease and the Neurobiology of Axons.* Annals of neurology, 2010. 67 (6): p. 715-725.
3. Morgan, J., *Joy of super smeller: sebum clues for PD diagnostics.* The Lancet Neurology. 15 (2): p. 138-139.
4. Wood-Kaczmar, A., S. Gandhi, and N. Wood, *Understanding the molecular causes of Parkinson's disease.* Trends in molecular medicine, 2006. 12 (11): p. 521-528.
5. Krestin, D., *The Seborrhoeic Facies as a Manifestation of Post-Encephalitic Parkinsonism and Allied Disorders.* QJM: An International Journal of Medicine, 1927. os-21 (81): p. 177-186.
6. Donadio, V., et al., *Skin nerve alpha-synuclein deposits: a biomarker for idiopathic Parkinson disease.* Neurology, 2014. 82 (15): p. 1362-9.
7. Shirasu, M. and K. Touhara, *The scent of disease: volatile organic compounds of the human body related to disease and disorder.* The Journal of Biochemistry, 2011. 150 (3): p. 257-266.
8. Pizzini, A., et al., *Analysis of volatile organic compounds in the breath of patients with stable or acute exacerbation of chronic obstructive pulmonary disease.* Journal of breath research, 2018.
9. Ishibe, A., et al., *Detection of gas components as a novel diagnostic method for colorectal cancer.* Annals of Gastroenterological Surgery, 2018.
10. Chang, J.-E., et al., *Analysis of volatile organic compounds in exhaled breath for lung cancer diagnosis using a sensor system.* Sensors and Actuators B: Chemical, 2018. 255: p. 800-807.
11. Lawal, O., et al., *Headspace volatile organic compounds from bacteria implicated in ventilator-associated pneumonia analysed by TD-GC/MS.* Journal of breath research, 2018. 12 (2): p. 026002.
12. Rattray, N. J. W., et al., *Taking your breath away: metabolomics breathes life in to personalized medicine.* Trends in Biotechnology, 2014. 32 (10): p. 538-548.
13. Xie, J., et al., *Analysis of changes in volatile constituents and expression of genes involved in terpenoid metabolism in oleocellosis peel.* Food chemistry, 2018. 243: p. 269-276.
14. Gatzias, I., et al., *Characterization and differentiation of sheep's milk from Greek breeds based on physicochemical parameters, fatty acid composition and volatile profile.* Journal of the Science of Food and Agriculture, 2018.
15. Gerhardt, N., et al., *Volatile Compound Fingerprinting by Headspace Gas Chromatography-Ion Mobility Spectrometry (HS-GC-IMS) for the Authenticity Assessment of Honey as Benchtop Alternative to 1H-NMR Profiling.* Analytical chemistry, 2018.
16. Liu, T., et al., *An Electronic Nose Based Beverage Identification using an Improved Fisher Discriminate Analysis Method.*
17. Abedi, G., Z. Talebpour, and F. Jamechenarboo, *The survey of analytical methods for sample preparation and analysis of fragrances in cosmetics and personal care products.* TrAC Trends in Analytical Chemistry, 2018.
18. Rosier, E., et al., *Development and validation of a new TD-GC/MS method and its applicability in the search for human and animal decomposition products.* Analytical and bioanalytical chemistry, 2014. 406 (15): p. 3611-3619.
19. Sariol, H. C., et al., *Characterization of the exhaustion profile of activated carbon in industrial rum "filters" based on TGA, TD-GC/MS, colorimetry and NMR relaxometry.* Materials Today Communications, 2017. 11: p. 1-10.
20. Herrington, J. S. and C. Myers, *Electronic cigarette solutions and resultant aerosol profiles.* Journal of chromatography A, 2015. 1418: p. 192-199.
21. Dunn, W. B., et al., *Systems level studies of mammalian metabolomes: the roles of mass spectrometry and nuclear magnetic resonance spectroscopy.* Chem Soc Rev, 2011. 40 (1): p. 387-426.
22. Goodacre, R., et al., *Proposed minimum reporting standards for data analysis in metabolomics.* Metabolomics, 2007. 3 (3): p. 231-241.
23. Wikoff, W. R., et al., *Metabolomics analysis reveals large effects of gut microflora on mammalian blood metabolites.* Proceedings of the National Academy of Sciences, 2009. 106 (10): p. 3698-3703.

What is claimed is:

1. A method of assessing whether an individual has Parkinson's Disease (PD) or whether an individual having PD is no longer responding to treatment for PD and treating the individual if they are determined to have PD or to be no longer responding to treatment for PD, the method comprising:
    identifying one or more volatile compounds in the sebum of the individual, wherein the one or more volatile compounds comprise one or more compounds selected from the following: eicosane, hippuric acid, octadecanal, perillic aldehyde, a cardiolipin and/or a glycolipid;
    determining that an individual has PD or that an individual having PD is no longer responding to treatment for PD if perillic aldehyde is reduced; hippuric acid is elevated; eicosane is elevated; octadecanal is elevated; the cardiolipin is reduced and/or the glycolipid is reduced with reference to a control sebum value; and
    if the individual is determined to have PD or is an individual having PD and is determined to be no longer responding to treatment for PD, administering a therapeutically effective amount of a neuroprotective agent to the individual.

2. The method as claimed in claim 1, wherein the method is for assessing whether an individual has early onset Parkinson's Disease (PD).

3. The method as claimed in claim 1, wherein the volatile compounds in the sebum are extracted using methanol.

4. The method as claimed in claim 1, wherein the method of identification is by mass spectrometry.

5. The method as claimed in claim 4, wherein the mass spectrometry comprises ambient ionization mass spectrometry.

6. The method as claimed in claim 5, wherein the ambient ionization mass spectrometry comprises paper spray mass spectrometry.

7. The method as claimed in claim 4, wherein the mass spectrometry is undertaken at a mass region in the range of 800 m/z to 2500 m/z.

\* \* \* \* \*